(12) United States Patent
Bakker et al.

(10) Patent No.: US 8,907,163 B2
(45) Date of Patent: Dec. 9, 2014

(54) TRANSGENIC PLANTS EXPRESSING GALACTOSYLTRANSFERASE AND SIALYL TRANSFERASE

(75) Inventors: Hendrikus Antonius Cornelis Bakker, Hannover (DE); Hendrik Jan Bosch, Wageningen (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 26 days.

(21) Appl. No.: 13/458,083

(22) Filed: Apr. 27, 2012

(65) Prior Publication Data

US 2012/0237972 A1 Sep. 20, 2012

Related U.S. Application Data

(60) Division of application No. 12/838,162, filed on Jul. 16, 2010, now Pat. No. 8,193,415, which is a continuation of application No. 11/704,055, filed on Feb. 8, 2007, now Pat. No. 7,781,647, which is a continuation of application No. 10/111,361, filed as application No. PCT/NL00/00775 on Oct. 26, 2000, now abandoned.

(30) Foreign Application Priority Data

Oct. 26, 1999 (EP) .................................. 99203523
Oct. 26, 1999 (EP) .................................. 99203524

(51) Int. Cl.
*C12N 15/82* (2006.01)
*A01H 5/00* (2006.01)
*C12N 9/10* (2006.01)

(52) U.S. Cl.
CPC .......... *C12N 9/1051* (2013.01); *C12N 15/8258* (2013.01); *C12N 15/8257* (2013.01)
USPC ........... 800/288; 800/295; 800/298; 435/419; 435/468

(58) Field of Classification Search
None
See application file for complete search history.

(56) References Cited

U.S. PATENT DOCUMENTS

| | | | |
|---|---|---|---|
| 4,956,282 A | 9/1990 | Goodman et al. | |
| 5,202,422 A | 4/1993 | Hiatt et al. | |
| 5,639,947 A | 6/1997 | Hiatt et al. | |
| 5,874,271 A | 2/1999 | Nishikawa et al. | |
| 5,879,912 A | 3/1999 | Roth | |
| 5,939,288 A | 8/1999 | Thornburg | |
| 5,959,177 A | 9/1999 | Hein et al. | |
| 6,046,040 A | 4/2000 | Nishiguchi et al. | |
| 6,054,304 A | 4/2000 | Taniguchi et al. | |
| 6,331,418 B1 | 12/2001 | Roth | |
| 6,344,600 B1 | 2/2002 | Merot et al. | |
| 6,388,068 B1 | 5/2002 | Satoh et al. | |
| 6,602,684 B1 | 8/2003 | Umana et al. | |
| 6,653,459 B1 | 11/2003 | Von Schaewen et al. | |
| 6,998,267 B1 | 2/2006 | Seki et al. | |
| 7,388,081 B2 | 6/2008 | Seki et al. | |
| 7,601,891 B2 | 10/2009 | Bakker et al. | |
| 7,741,539 B2 * | 6/2010 | Gorr et al. | 800/298 |
| 7,781,647 B2 | 8/2010 | Bakker et al. | |
| 7,897,842 B2 | 3/2011 | Bakker et al. | |
| 8,058,508 B2 | 11/2011 | Bakker et al. | |
| 8,106,169 B2 | 1/2012 | Briggs et al. | |
| 8,193,415 B2 | 6/2012 | Bakker et al. | |
| 8,241,909 B2 | 8/2012 | Seki et al. | |
| 8,309,795 B2 | 11/2012 | Fujiyama et al. | |
| 2001/0055584 A1 | 12/2001 | McKenzie et al. | |
| 2002/0019342 A1 | 2/2002 | Bayer | |
| 2002/0174453 A1 | 11/2002 | Danielle et al. | |
| 2004/0072290 A1 | 4/2004 | Umana et al. | |
| 2004/0181827 A1 | 9/2004 | Schaewen et al. | |
| 2004/0214273 A1 | 10/2004 | Fujiyama et al. | |
| 2005/0143564 A1 | 6/2005 | Seki et al. | |
| 2005/0144670 A1 | 6/2005 | Fujiyama et al. | |
| 2005/0223430 A1 | 10/2005 | Bakker et al. | |
| 2006/0253928 A1 | 11/2006 | Bakker et al. | |
| 2007/0089201 A1 | 4/2007 | Briggs et al. | |
| 2007/0214519 A1 | 9/2007 | Fujiyama et al. | |
| 2008/0003680 A1 | 1/2008 | Bakker et al. | |
| 2008/0034456 A1 | 2/2008 | Fujiyama et al. | |
| 2008/0124798 A1 | 5/2008 | Seki et al. | |
| 2010/0122365 A1 | 5/2010 | Bakker et al. | |

(Continued)

FOREIGN PATENT DOCUMENTS

AU 1681300 6/2000
DE 19754622 6/1999

(Continued)

OTHER PUBLICATIONS

Castilho et al. In planta protein sialylation through overexpression of the respective mammalian pathway. (2010) Journal of Biological Chemistry; vol. 285; pp. 15923-15930.*
Paccalet et al. Engineering of a sialic acid synthesis pathway in transgenic plants by expression of bacterial Neu4Ac-synthesizing enzymes. (2007) Plant Biotechnology Journal; vol. 5; pp. 16-25.*
GENBANK Submission; NIH/NCBI, Accession No. AJ277603. Bakker et al. Apr. 28, 2000.
GENBANK Submission; Accession No. Q92074. Shaper J.H. Nov. 1, 1996.
GENBANK Submission; Accession No. ADL27179. Hillman J. L. et al. May 20, 2004.
GENBANK Submission; Accession No. U19890. Shaper J. H. Aug. 3, 1996.

(Continued)

*Primary Examiner* — Cathy Kingdon Worley
(74) *Attorney, Agent, or Firm* — Wolf, Greenfield & Sacks, P.C.

(57) ABSTRACT

The invention relates to the field of glycoprotein processing in transgenic plants used as cost efficient and contamination safe factories for the production of recombinant biopharmaceutical proteins or pharmaceutical compositions comprising these. The invention provides a plant comprising functional mammalian β1,4-galactosyltransferase and mammalian sialyl transferase for producing complex N-linked glycans that are galactosylated and sialylated, said plant additionally comprising at least a second mammalian protein or functional fragment thereof that is normally not present in plants.

13 Claims, 6 Drawing Sheets

(56) References Cited

U.S. PATENT DOCUMENTS

Figure 1:
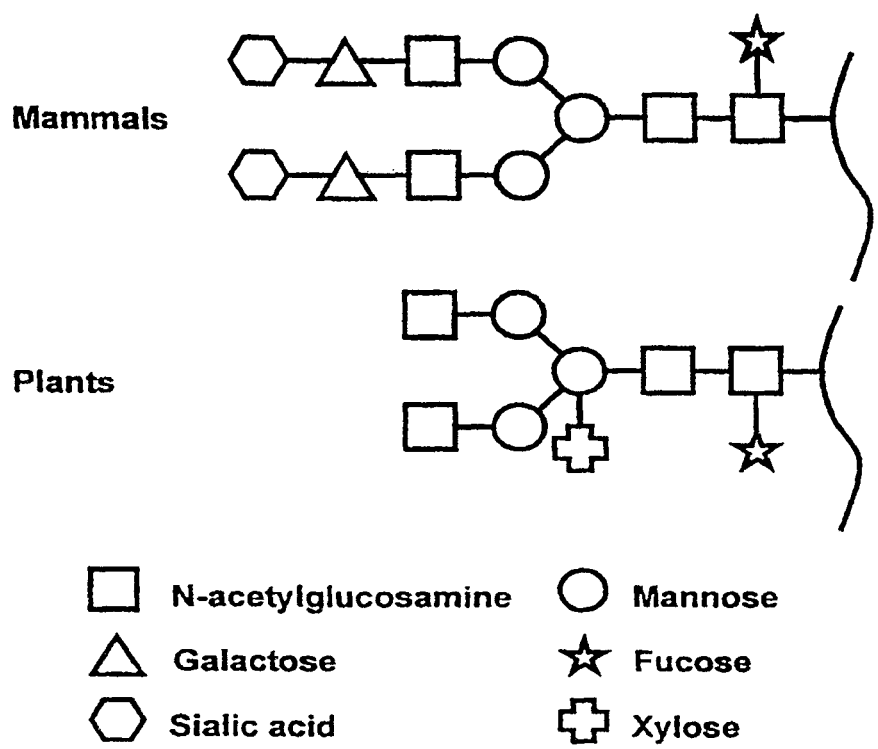

| | | |
|---|---|---|
| 2011/0030108 A1 | 2/2011 | Bakker et al. |
| 2011/0067146 A1 | 3/2011 | Rouwendal et al. |
| 2011/0070649 A1 | 3/2011 | Seki et al. |
| 2012/0010155 A1 | 1/2012 | Bakker et al. |
| 2012/0011600 A1 | 1/2012 | Bakker et al. |
| 2012/0036596 A9 | 2/2012 | Rouwendal et al. |
| 2012/0060239 A1 | 3/2012 | Fujiyama et al. |
| 2012/0210466 A9 | 8/2012 | Rouwendal et al. |
| 2013/0040391 A1 | 2/2013 | Seki et al. |

FOREIGN PATENT DOCUMENTS

| | | |
|---|---|---|
| EP | 0 351 313 A2 | 1/1990 |
| EP | 0 550 756 A1 | 7/1993 |
| EP | 0 737 745 A1 | 10/1996 |
| EP | 0 816 503 A1 | 1/1998 |
| EP | 1 243 647 A1 | 9/2002 |
| JP | S54-055790 | 5/1979 |
| JP | S56-016496 | 2/1981 |
| JP | S56-053696 | 5/1981 |
| JP | S56-108798 | 8/1981 |
| JP | S57-149228 | 9/1982 |
| JP | S57-169424 | 10/1982 |
| JP | H10-313617 | 12/1998 |
| JP | 2000-245470 | 9/2000 |
| JP | 2000-287692 | 10/2000 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |
| WO | WO 97/04122 | 2/1997 |
| WO | WO 98/31826 | 7/1998 |
| WO | WO 98/31828 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/28792 A2 | 5/2000 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 | 5/2001 |
| WO | WO 01/49821 | 7/2001 |
| WO | WO 01/49831 | 7/2001 |
| WO | WO 01/62912 | 8/2001 |
| WO | WO 01/64901 | 9/2001 |
| WO | WO 01/81591 | 11/2001 |
| WO | WO 01/82912 | 11/2001 |
| WO | WO 02/00879 | 1/2002 |
| WO | WO 02/057468 | 7/2002 |
| WO | WO 02/070672 | 9/2002 |
| WO | WO 03/011878 | 2/2003 |
| WO | WO 03/076614 | 9/2003 |
| WO | WO 03/078614 | 9/2003 |
| WO | WO 03/078637 | 9/2003 |
| WO | WO 2004/050838 | 6/2004 |

OTHER PUBLICATIONS

GENBANK Submission; Accession No. BC124813. Aug. 5, 2006.
GENBANK Submission; Accession No. Q08B99. Strausberg et al. Oct. 31, 2006.
Aoki et al. Golgi retention of a trans-Golgi membrane protein, galactosyl-transferase, requires cysteine and histidine residues within the membrane-anchoring domain. (1992) Cell Biology 89, 4319-4323.
Asano et al., Growth retardation and early death of beta-1,4-galactosyltransferase knockout mice with augmented proliferation and abnormal differentiation of epithelial cells. EMBO J. Apr. 15, 1997;16(8):1850-7.
Bailey et al. Metabolic engineering of N-linked glycoform synthesis systems in Chinese hamster ovary (CHO) cells (1997) Animal Cell Technology, pp. 489-494.
Bakker et al., Galactose-extended glycans of antibodies produced by transgenic plants. Proc Natl Acad Sci U S A. Feb. 27, 2001;98(5):2899-904.
Bakker et al., An Arabidopsis thaliana Cdna complements the N-acetylglucosaminyltransferase I deficiency of CHO Lec1 cells. Biochem Biophys Res Commun. Aug. 11, 1999;261(3):829-32.
Bakker et al., Expression cloning of a cDNA encoding a sulfotransferase involved in the biosynthesis of the HNK-1 carbohydrate epitope. J Biol Chem. Nov. 21, 1997;272(47):29942-6.
Borisjuk et al., Production of Recombinant Proteins in Plant Root Exudates. Nat. Biotechnology 17(5): 466-469 (1999).
Bosch et al., A trout growth hormone is expressed, correctly folded and partially glycosylated in the leaves but not the seeds of transgenic plants. Transgenic Res. 1994 (month not listed on publication). 3:304-10.
Boyd et al. The effect of the removal of sialic acid, galactose and total carbohydrate on the functional activity of Campath-1H (1995) Mol Imm. 32, 1311-8.
Cabanes-Macheteau et al., N-Glycosylation of a mouse IgG expressed in transgenic tobacco plants. Glycobiology. Apr. 1999;9(4):365-72.
Choi et al., Use of combinatorial genetic libraries to humanize N-linked glycosylation in the yeast *Pichia pastoris*. Proc Natl Acad Sci U S A. Apr. 29, 2003;100(9):5022-7. Epub Apr. 17, 2003.
Chrispeels, M., Glycobiology of Plant Cells, Essentials of Glycobiology, Ch. 20; Varki et al., 1st ed. (1999) Cold Spring Harbor Laboratory Press, NY.
Chrispeels and Faye, The production of recombinant glycoproteins with defined non-immunogenic glycans. In: Transgenic plants: a production system for industrial and pharmaceutical proteins. John Wiley Pub, UK. 1996:99-113.
Colley Golgi localization of glycosyltransferases: more questions than answers. (1997) Glycobiology 7(1):1-13.
Cousin et al. Human variant sex hormone-binding globulin (SHBG) with an additional carbohydrate chain has a reduced clearance rate in rabbit. (1998) J of Clin. Endocrin. And Metab. 83: 235-240.
Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.
De Vries et al. Isolation of total and polysomal RNA from plant tissues. (1991) Plant Mol. Biology B6/1-13.
Dieryck et al. Human Haemoglobin from transgenic tobacco (1997) Nature 386, 29-30.
Dinter and Berger, The regulation of cell- and tissue-specific expression of glycans by glycosyltransferases. Adv Exp Med Biol. 1995;376:53-82.
Elbers et al., Influence of growth conditions and developmental stage on N-glycan heterogeneity of transgenic immunoglobulin G and endogenous proteins in tobacco leaves. Plant Physiol. Jul. 2001;126(3):1314-22.
Essl et al., The N-terminal 77 amino acids from tobacco N-acetylglucosaminyltransferase I are sufficient to retain a reporter protein in the Golgi apparatus of *Nicotiana benthamiana* cells. FEBS Lett. Jun. 18, 1999;453(1-2):169-73.
Fast et al., The role of the carbohydrate chains of Gal beta-1,4-GlcNAc alpha 2,6-sialyltransferase for enzyme activity. Biochim Biophys Acta. Oct. 6, 1993;1202(2):325-30.
Faye et al., Affinity purification of antibodies specific for Asn-linked glycans containing alpha 1—>3 fucose or beta —>2 xylose. (1993) Anal Biochem 209, 104-8.
Fischer and Evans, Molecular farming of pharmaceutical proteins. Transgenic Research. 2000;9:279-299.
Fischer et al., Molecular farming of recombinant antibodies in plants. (1999) Biol. Chem. 380: 825-839.

(56) References Cited

OTHER PUBLICATIONS

Fitchette-Laine et al., Chapter 19: Analysis of *N*- and *O*-Glycosylation of plant proteins. Methods in Biotechnology, vol. 3. Cunningham and Porter, eds. Humana Press. 1998: 271-90.

Fitchette Laine et al. N-glycans harboring the Lewis a epitope are expressed at the surface of plant cells. (1997) Plan J 12, 1411-7.

Florack et al., Expression of giant silkmoth cecropin B genes in tobacco. (1995) Transgenic Research 4, 132-141.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Fujiyama et al., In vivo conversion of a glycan to human compatible type by transformed tobacco cells. Biochem Biophys Res Commun. Nov. 30, 2001;289(2):553-7.

Gasser and Fraley, Genetically Engineering Plants for Crop Improvement. Science. Jun. 16, 1989;244(4910):1293-1299.

Giddings, Transgenic plants as protein factories. Curr Opin Biotechnol. Oct. 2001;12(5):450-4.

Gleeson, Targeting of proteins to the Golgi apparatus. (1998) Histochem Cell Biol. 109: 517-532.

Gomez and Chrispeels, Complementation of an *Arabidopsis thaliana* mutant that lacks complex asparagine-linked glycans with the human cDNA encoding N- acetylglucosaminyltransferase I. Proc Natl Acad Sci U S A. Mar. 1, 1994;91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman and Horvitz, Three proteins involved in *Caenorhabditis elegans* vulval invagination are similar to components of a glycosylation pathway. Proc Natl Acad Sci U S A. Feb. 2, 1999;96(3):974-9.

Hein et al., Evaluation of immunoglobulins from plant cells. Biotechnol Prog. Sep.-Oct. 1991;7(5):455-61.

Hess et al., Transformation experiments by pipetting *Agrobacterium* into the spikelets of wheat (*Triticum aestivum* L.). Plant Science 1990;72:233-44.

Hiatt et al., Monoclonal antibody engineering in plants. FEBS Lett. Jul. 27, 1992;307(1):71-5.

Hiei et al., Efficient transformation of rice (*Oryza sativa* L.) mediated by Agrobacterium and sequence analysis of the boundaries of the T-DNA. Plant J. Aug. 1994;6(2):271-82.

Hiei et al., Transformation of rice mediated by *Agrobacterium tumefaciens*. Plant Mol Biol. Sep. 1997;35(1-2):205-18.

Hollister et al. Stable expression of mammalian β1,4-galactosyltransferase extends the N-glycosylation pathway in insect cells. (1998) Glycobiology 8(5): 473-480.

Hollister et al., Engineering the protein N-glycosylation pathway in insect cells for production of biantennary, complex N-glycans. Biochemistry. Dec. 17, 2002;41(50):15093-104.

Horsch et al. A simple and general method for transferring genes into plants. (1985) Science 227, 1229-1231.

Huether et al., Glyco-engineering of moss lacking plant-specific sugar residues. Plant Biol (Stuttg). May 2005;7(3):292-9.

Ihara et al., cDNA cloning, expression, and chromosomal localization of human N-acetylglucosaminyltransferase III (GnT-III). J Biochem (Tokyo). Jun. 1993;113(6):692-8.

Ihara et al ., Ectopic Expression of N-acetylglucosaminyltransferase III in transgenic hepatocytes disrupts apolipoprotein B secretion and induces aberrant cellular morphology with lipid storage. Proc Natl Acad Sci USA 1998 95:2526-2530.

Ikeda et al., Kinetic basis for the donor nucleotide-sugar specificity of betal, 4-N-acetylglucosaminyltransferase III. J Biochem. Oct. 2000;128(4):609-19.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by *Agrobacterium tumefaciens*. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif. Jun. 2000;19(1):131-8.

Jarvis and Finn, Modifying the insect cell N-glycosylation pathway with immediate early baculovirus expression vectors. (1996) Nat Biotechnol 14, 1288-92.

Jenkins et al., Getting the glycosylation right: implications for the biotechnology industry. Nat Biotechnol. Aug. 1996;14(8):975-81.

Johnson and Chrispeels, Substrate specificities of N-acetylglucosaminyl-, fucosyl-, and xylosyltransferases that modify glycoproteins in the Golgi apparatus of bean cotyledons. (1987) Plant Physiology 84, 1301-1308.

Kakuda et al., Purification and characterization of two recombinant human glucuronyltransferases involved in the biosynthethis of HNK-1 carbohydrate in *Escherichia coli* (2004). Protein Expression and Purification; vol. 35 ; pp. 111-119.

Kang et al., Salt tolerance of *Arabidopsis thaliana* requires maturation of N-glycosylated proteins in the Golgi apparatus. PNAS 2008 105(15):5933-5938.

Kawar et al., Insect cells encode a class II alpha-mannosidase with unique properties. J Biol Chem. May 11, 2001;276(19):16335-40. Epub Feb. 9, 2001.

Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.

Kihlberg et al., Glysocylated peptide hormones: pharmacological properties and conformation studies of analogues of [1-Desamino,8-D-arginine]vasopressin. J. Med. Chem. 1995; 38:161-169.

Kitagawa et al., Molecular cloning and expression of glucuronyltransferase I involved in the biosynthesis of the glycosaminoglycan-protein linkage region of proteoglycans. (1998) JBC 273:6615-6618.

Kleene et al., Expression of soluble active human beta 1,4 galactosyltransferase in *Saccharomyces cerevisiae*. Biochem Biophys Res Commun. May 30, 1994;201(1):160-7.

Krezdorn et al., Human beta 1,4 galactosyltransferase and alpha 2,6 sialyltransferase expressed in *Saccharomyces cerevisiae* are retained as active enzymes in the endoplasmic reticulum. Eur J Biochem. Mar. 15, 1994;220(3):809-17.

Ku et al., High-level expression of maize phosphoenolpyruvate carboxylase in transgenic rice plants. Nat Biotechnol. Jan. 1999;17(1):76-80.

Leiter et al., Purification, cDNA cloning, and expression of GDP-L-Fuc:Asn-linked GlcNAc alpha1,3-fucosyltransferase from mung beans. J Biol Chem. Jul. 30, 1999;274(31):21830-9.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.

Lerouge et al., N-glycoprotein biosynthesis in plants: recent developments and future trends. Plant Mol Biol. Sep. 1998;38(1-2):31-48.

Lerouge et al., N-glycosylation of recombinant pharmaceutical glycoproteins produced in transgenic plants: towards an humanisation of plant N-glycans. Curr Pharm Biotechnol. Dec. 2000;1(4):347-54.

Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001; 268(21):5653.

(56) References Cited

OTHER PUBLICATIONS

Ma et al. Generation and assembly of secretory antibodies in plants (1995) Science 268, 716-9.
Madson et al., Altered xyloglucans of arabidopsis thalianamutants bind normally to cellulose in vivo and in vitro. Poster from Plant Biology(Rockville) Jul. 27, 2001 Abstract #527.
Magnuson et al., Secretion of biologically active human interleukin-2 and interleukin-4 from genetically modified tobacco cells in suspension culture. Protein Expr Purif. Jun. 1998;13(1):45-52.
Magnuson et al., Enhanced recovery of a secreted mammalian protein from suspension culture of genetically modified tobacco cells. Protein Expr Purif. Mar. 1996;7(2):220-8.
Maras et al., In vitro conversion of the carbohydrate moiety of fungal glycoproteins to mammalian-type oligosaccharides—evidence for N-acetylglucosaminyltransferase-I-accepting glycans from *Trichoderma reesei*. Eur J Biochem. Nov. 1, 1997;249(3):701-7.
Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.
Matsumoto et al., Characterization of a human glycoprotein (erythropoietin) produced in cultured tobacco cells. Mol. Biol. 1995; 27, 1163-1172.
Melo et al. Identification of the human Lewis(a) carbohydrate motif in a secretory peroxidase from a plant cell suspension culture (*Vaccinium myrtillus* L.) FEBS Lett. 1997; 415, 186-91.
Milland et al., The cytoplasmic tail of α1,2-fucosyltransferase contains a sequence for golgi localization. (2001) J. Biol. Chem. 276(15):12012-12018.
Miyake et al., Purification of human erythropoietin. J Biol Chem. Aug. 10, 1977;252(15):5558-64.
Miyoshi et al., The alpha1-6-fucosyltransferase gene and its biological significance. Biochim Biophys Acta. Dec. 6, 1999;1473(1):9-20.
Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.
Munro, Localization of proteins to the Golgi apparatus. (1998) Trends Cell Biol. 8(1): 11-15.
Nagai et al., N-Glycosylation is Requisite for the Enzyme Activity and Golgi Retention of N-Acetylglucosaminyltransferase III. Glycobiology 7(6):769-776 (1997).
Paccalet et al., Engineering of a sialic acid synthesis pathway in transgenic plants by expression of bacterial Neu5Ac-synthesizing enzymes. Plant Biotechnol J. Jan. 2007;5(1):16-25.
Palacpac et al., Stable expression of human beta1,4-galactosyltransferase in plant cells modifies N-linked glycosylation patterns. Proc Natl Acad Sci U S A. Apr. 13, 1999;96(8):4692-7.
Palacpac et al., Structures of N-linked oligosaccharides of glycoproteins from tobacco BY2 suspension cultured cells. Biosci Biotechnol Biochem. Jan. 1999;63(1):35-9.
Philipp et al., Characterization of nuclear membranes and endoplasmic reticulum isolated from plant tissue. JCB 1976 68:11-29.
Rayon et al., Characterization of N-Glycans from Arabidopsis. Application to a Fucose-Deficient Mutant (1999) Plant Physiology 119, 725-733.
Rayon et al., N-Glycosylation of phytohemagglutinin expressed in bean cotyledons or in transgenic tobacco plants. Plant Physiol Biochem. 1996;34:273-81.
Rayon et al., The protein N-glycosylation in plants. Journal Exper Botany. Sep. 1998. 49(326):1463-72.
Rishi et al., Molecular Farming in Plants: A Current Perspective. (2001) J. Plant Biochem. & Biotech 10: 1-12.
Rothman, Protein sorting by selective retention in the endoplasmic reticulum and Golgi stack. Cell. Aug. 14, 1987;50(4):521-2.
Saint-Jore-Dupas et al., Plant N-Glycan Processing Enzymes Employ Different Targeting Mechanisms for Their Spatial Arrangement along the Secretory Pathway. The Plant Cell. 2006 18:3182-3200.
Saito et al., Integration and expression of a rabbit liver cytochrome P-450 gene in transgenic *Nicotiana tabacum*. (1991) Proc. Natl. Acad. Sci. 88, 7041-7045.
Sakai et al., Fatty Acid acylation of apoE by human monocyte/marophages and helptocytes. Apr. 1998; 417. Abstract.
Sakai et al., Human glycosyltransferase expression and intracellular/intercellular glycoprotein sugar chain structure in cultured tobacco BY2 cells. IC Biotech. Osaska, Nara Institute. Mar. 1998. Abstract. Original with English Abstract.
Sakai et al., Human glycosyltransferase expression and intracellular/intercellular glycoprotein sugar chain structure in cultured tobacco BY2 cells. Corrected title: Expression of human β 1,4-galactosyltransferase in tobacco BY2 cells modifies glycosylation patterns of intracellular and extracellular glycoproteins. IC Biotech. Osaska, Nara Institute. Mar. 1998. Abstract.
Sakai et al., Expression of Human β 1,4-Galactosyltransferase in Tobacco BY2 Cells Modifies Glycosylation Patterns of Intracellular and Extracellular Glycoproteins. Translation of Abstract from the Ann. Meeting of Japan Society for Bioscience, Biotechnology, and Agrochemistry, Published Mar. 1998. (Additional translation of Sakai et al previously submitted).
Schachter, The 'yellow brick road' to branched complex N-glycans. Glycobiology. Nov. 1991;1(5):45-61.
Scherer et al., Action and Inhibition of Endogenous Phospholipases during Isolation of Plant Membranes. Plant Physiol 1978 62:933-37.
Schindler et al., Arabinogalactan proteins in maize coleoptiles: developmental relationship to cell death during xylem differentiation but not to extention growth. (1995) Plant JU 7, 25-36.
Seveno et al., Glycoprotein Sialylation in plants? Nat Biotechnol. Nov. 2004;22(11):1351-2.
Shah et al., Sialylated endogenous glycoconjugates in plant cells. Nat Biotechnol. Dec. 2003;21(12):1470-1. Epub Nov. 9, 2003.
Shaper et al., Bovine galactosyltransferase: identification of a clone by direct immunological screening of a cDNA expression library. (1986) Proc Natl Acad Sci USA v83, 1573-7.
Smant et al., Potato root diffusate- induced secretion of soluble, basic proteins originating from the subventral esophageal glands of potato cyst nematodes (1997) Phytopathology v87, 839-845.
Stanley et al., Glycosyltransferase mutants: key to new insights in glycobiology. FASEB J. 1995;9:1436-44.
Stanley et al., CHO cells provide access to novel N-glycans and developmentally regulated glycosyltransferases. Glycobiology. 1996;6:695-9.
Staudacher E, "Functional purification and characterization of a GDP-fucose: beta-N-acetylglucosamine (Fuc to Asn linked GlcNAc) alpha 1,3-fucosyltransferase from mung beans." Glycoconj J. Dec. 1995;12(6):780-6.
Staudacher, Strict order of (Fuc to Asn-linked GlcNAc) fucosyltransferases forming core-difucosylated structures. Glycoconj J. Apr. 1998;15(4):355-60.
Strasser et al., Molecular cloning of cDNA encoding N-acetylglucosaminyltransferase II from *Arabidopsis thaliana*. Glycoconj J. Dec. 1999;16(12):787-91.
Strasser et al., Molecular cloning and functional expression of beta 1,2-sylosyltransferase cDNA from *Arabidopsis thalianal*. Febs Letters, Elsevier, Amsterdam, NL, Apr. 2000 472(1): 105-108.
Strasser et al., Molecular basis of N-acetylglucosaminyltransferase I deficiency in *Arabidopsis thaliana* plants lacking complex N-glycans. Biochem J. Apr. 15, 2005;387(Pt 2):385-91. Epub Nov. 10, 2004.
Sturm et al., Subcellular localization of glycosidases and glycosyltransferases involved in the processing of N-linked oligosaccharides. (1987) Plant Physiol. 85(3):741-745.
Takahashi et al., Xylose-containing common structural unit in N-linked oligosaccharides of laccase from sycamore cells. Biochemistry. 1986;25(2):388-95.
Tang et al., The transmembrane domain of N-glucosaminyltransferase I contains a Golgi retention signal. J Biol Chem. May 15, 1992;267(14):10122-6.

(56) References Cited

OTHER PUBLICATIONS

Taniguchi et al., A glycomic approach to the identification and characterization of glycoprotein function in cells transfected with glycosyltransferase genes. Proteomics. Feb. 2001;1(2):239-47.
Terashima et al., Effect of Osmotic Pressure on Human αl-Antitrypsin Production by Plant Cell Culture. Biochemical Engineering Journal 4 (1999) 31-36.
Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.
Terayama et al., Purification and characterization of a glucuronyltransferase involved in the biosynthesis of the HNK-1 epitope on glycoproteins from rat brain. J Biol Chem. Nov. 13, 1998;273(46):30295-30300.
Thanavala et al., Immunogenicity of transgenetic plant derived hepatitis B surface antigen.(1995) Proc Natl Acad Sci USA 92, 3358-3361.
Udagama-Randeniya et al., Electrophoretic analysis of coniferyl alcohol oxidase and related laccases. Electrophoresis. Aug.-Sep. 1994;15(8-9):1072-7.
Umana et al., Engineered glycoforms of an antineuroblastoma IgG1 with optimize antibody-dependent cellular cytotoxic activity. (1999) Nature Biotech. 17: 176-180.
Van Engelen et al., Coordinate expression of antibody subunit genes yields high levels of functional antibodies in roots of transgenic tobacco. Plant Mol Biol. Dec. 1994; 26(6):1701-10.
Van Engelen et al., pBINPLUS: an improved plant transformation vector based on pBIN19. (1995) Transgenetic Res 4, 288-90.
Van Ree et al., Beta(1,2)-xylose and alpha(1,3)-fucose residues have a strong contribution in IgE binding to plant glycoallergens. J Biol Chem. Apr. 14, 2000;275(15):11451-8.
Vitale and Chrispeels, Transient N-acetylglucosamine in the biosynthesis of phytohemagglutinin: attachment in the Golgi apparatus and removal in protein bodies. J Cell Biol. Jul. 1984;99(1 Pt 1):133-40.
Voelker et al., In vitro mutated phytohemagglutinin genes expressed in tobacco seeds: role of glycans in protein targeting and stability. Plant Cell. Jan. 1989;1(1):95-104.
Von Schaewen et al. Isolation of a mutant arabidopsis plant that lacks N-acetyl glucosaminyl transferase I and is unable to synthesize Golgi-modified complex N-linked glycans. (1993) Plant Physiol 102, 1109-18.
Warner, Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.
Wee et al., Targeting of active sialyltransferase to the plant Golgi apparatus. Plant Cell. Oct. 1998;10(10):1759-68.
Whitelam, The production of recombinant proteins in plants. (1995) J. Sci. Food Agric., 68:1-9.
Wiebauer et al., Nuclear pre-mRNA processing in plants: distinct modes of 3'splice-site selection in plants and animals (1988) MCB: vol. 8 pp. 2042-2051.
Wilson et al., Core alpha1 ,3-fucose is a key part of the epitope recognized by antibodies reacting against plant N-linked oligosaccharides and is present in a wide variety of plant extracts. Glycobiology. Jul. 1998;8(7):651-61.
Wilson et al., Cloning and expression of cDNAs encoding alpha1,3-fucosyltransferase homologues from *Arabidopsis thaliana*. Biochim Biophys Acta. Jul. 2, 2001;1527(1-2):88-96.
Wright and Morrison, Effect of glycosylation on antibody function: implications for genetic engineering. Trends Biotechnol. Jan. 1997;15(1):26-32.
Yamaguchi et al., Genomic structure and promoter analysis of the human alpha1, 6-fucosyltransferase gene (FUT8). Glycobiology. Jun. 2000;10(6):637-43.
Yamaguchi and Fukuda, Golgi retention mechanism of β-1,4-Galactosyltransferase (1995) J of Biol Chemistry 270(20): 12170-12176.
Yin et al., [Obtaining transgenic rice plants and their progenies using *Agrobacterium tumefaciens*] Yi Chuan Xue Bao. Dec. 1998;25(6):517-24. Chinese. English abstract only.
Yoshida et al., Molecular biology and application of plant peroxidase genes. Appl Microbiol Biotechnol. Feb. 2003;60(6):665-70. Epub Dec. 18, 2002.
Yoshida et al., Expression of β1 4 galactosyltransferase in tobacco culture cell. Program for Congress of the Society for Bioscience and Bioengineering of Japan. Sep. 15, 1995;1-5.
Yosida et al., Challenge for production of human-compatible glycoprotein therapeutics in yeast. Bioscience and Industry. 1996;54(6): 420-422.
Zhang et al., Transformation of tobacco using human β-1 , 4 galactosyltransferase gene and regeneration of transgenic plants. Annual reports of IC Biotech. 1995;18:241-7.
Zhang et al., Agrobacterium-mediated transformation of elite indica and japonica rice cultivars. Mol Biotechnol. Dec. 1997;8(3):223-31.
Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.
Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.

\* cited by examiner

TRANSGENIC PLANTS EXPRESSING GALACTOSYLTRANSFERASE AND SIALYL TRANSFERASE

RELATED APPLICATIONS

This application is a divisional of U.S. application Ser. No. 12/838,162, filed on Jul 16, 2010, now U.S. Pat. No. 8,193,415, which is a continuation of U.S. Application Ser. No. 11/704,055, filed on Feb. 8, 2007, now U.S. Pat. No. 7,781,647, which is a continuation of U.S. application Ser. No. 10/111,361, filed Aug. 5, 2002, now abandoned, which is a national stage filing under 35 U.S.C. 371 of International Application PCT/NL00/00775, filed Oct. 26, 2000, which claims priority to European Application No. 99203524.6, filed Oct. 26, 1999 and European Application No. 99203523.8, filed Oct. 26, 1999, the entire contents of each of which are incorporated by reference herein.

The invention relates to the field of glycoprotein processing in transgenic plants used as cost efficient and contamination safe factories for the production of useful proteinaceous substances such as recombinant biopharmaceutical proteins or (pharmaceutical) compositions comprising these.

The creation of recombinant proteins as e.g. medicaments or pharmaceutical compositions by pharmaco-molecular agriculture constitutes one of the principal attractions of transgenic plants; it is also the domain where their utilization is accepted best by the public opinion. In addition to the yield and the favourable cost which may be expected from the field production of recombinant proteins, transgenic plants present certain advantages over other production systems, such as bacteria, yeasts, and animal cells. Indeed, they are devoid of virus which might be dangerous to humans, and can accumulate the proteins of interest in their "organs of storage", such as seeds or tubers. This facilitates their handling, their transportation and their storage at ambient temperature, while affording the possibility of subsequent extraction according to needs. Moreover, the transgenic plant, or some of its parts, can be utilised as vector of medicaments or of vaccines. In 1996, the team of Charles Arntzen (Boyce Thompson Institute for Plant Research, Cornell University, New York) has demonstrated the production of a recombinant vaccine against the thermolabile enterotoxin of *Escherichia coli* by the potato. Its efficacy has been demonstrated in mice and through clinical trials carried out on volunteers having consumed 50 to 100 grams of raw transgenic potatoes over a period of six months. Another team, at Loma Linda, in California, has successfully tested in mice a vaccine against cholera formed in the potato. Traditional vaccination against germs responsible for enteropathies is regarded as "too costly" to be generally implemented in developing countries. However, the production of oral vaccines for example no longer in the potato but in the banana, would, at a very low cost, enable general implementation of vaccination against diarrheas of bacterial origin, which cause the death of three million children every year. In the developed-countries, one can imagine that children would certainly prefer a banana or strawberry vaccine to the doctor's needle. More generally, molecular pharming could enable developing countries to produce, at low cost, substantial quantities of therapeutic proteins utilizing the capacities of their agriculture, without it being necessary to invest in pharmaceutical factories. Although the advantages of plants as factories of proteinaceous substances are explained mostly in the light of biopharmaceuticals, plants are also useful for production of other proteins, e.g. industrial enzymes and the like, because of their capability of glycosylation leading e.g. to higher stability.

Today, the utilisation of plants for the production of proteins or glycoproteins for therapeutic use has gone widely beyond the domain of science fiction since soy, tobacco, the potato, rice or rapeseed is the object of investigations for the production of vaccines, proteins or peptides of mammals such as: monoclonal antibodies, vaccine antigens, enzymes such as canine gastric lipase, cytokines such as epidermal growth factor, interleukins 2 and 4, erythropoietin, encephalins, interferon and serum albumin, for the greater part of human origin. Some of these proteins have already proven their efficacy in human volunteers, however, their potential immunogenicity and their possible allergenic character still restrict their development. Several heterologous proteins have successfully been produced in plants. Among these proteins are monoclonal antibodies, hormones, vaccine antigens, enzymes and blood proteins (Dieryck et al., 1997; Florack et al., 1995; Ma et al., 1995) Matsumoto et al., 1163; Saito et al., 1991; Thanavala et al. 1995) A major limitation of plants, shared with other heterologous expression systems like bacteria, yeast and insect cells, is their different glycosylation profile compared to mammals. In contrast to bacteria, having no N-linked glycans, and yeast, having only high mannose glycans, plants are able to produce proteins with complex N-linked glycans. Plant glycoproteins have complex N-linked glycans containing a α1,3 linked core fucose and β1,2 linked xylose residues not found in mammals (Lerouge et al., 1998) (FIG. 1). The core of plant N-glycans can, as in mammals, be substituted by 2 GlcNAc¹ residues, which are transferred by N-acetylglucosaminyltransferase I and II (Schachter, 1991) although their appearance varies (Rayon et al., 1999. N-glycans of some plant glycoproteins contain in addition a LewisA (Fucα1,4(Galβ1,3)GlcNAc) epitope (Fitchette Laine et al., 1997; Melo et al., 1997). However, plant glycoproteins lack the characteristic galactose (NeuAcα2,6Galβ1,4) containing complex N-glycans found in mammals, while also α1,6 linked core fucose is never found (FIG. 1; Schachter, 1991). A mouse monoclonal antibody produced in tobacco plants (Ma et al., 1995) has a typical plant N-glycosylation. 40% High-mannose glycans and 60% complex glycans containing xylose, fucose and 0, 1 or 2 terminal GlcNAc residues (Cabanes Macheteau et al., 1999).

In short, analyses of glycoproteins from plants have indicated that several steps in the glycosylation pathways of plants and mammals are very similar if not identical. There are however also clear differences, particularly in the synthesis of complex glycans. The complex glycans of plants are generally much smaller and contain beta-1,2 xylose or alpha-1,3 fucose residues attached to the Mani (GlcNAc)2 core. Such residues on glycoprotein are known to be highly immunogenic. This will cause problems for certain applications of recombinant proteins carrying these sugars. In addition, although common and often essential on mammalian glycoproteins, sialic acid has never been found in plant glycans. This is particularly relevant since experiments have shown, that the absence of terminal sialic acid on glycosidic side chains can dramatically decrease biological activity in vivo. Most likely, asialo-glycoprotein-receptors in the liver can bind to asialo-glycoprotein, and thereby cause a clearance of the glycoprotein from the circulation, which is reflected in a reduced metabolic half life and low bioactivity in vivo.

The invention provides a plant comprising a functional mammalian enzyme providing N-glycan biosynthesis that is normally not present in plants. It is especially the "plant" character of the glycans that makes glycoproteins produced in plants less suited for pharmaceutical use. This "plant" character imparts undesired antigenic and immunogenic characteristics to the glycoprotein in question, which would require a strategy intended to prevent immunogenicity of glycoproteins produced by transgenic plants. The aim of the strategy is to modify the genome of vegetable cells in such a manner that they ripen their proteins like human cells would. Numerous genes of glycosyl transferases of mammals have already been cloned, which is not the case in plants. In view of the ease of transformation of vegetable systems, the temptation is strong to "complement" the Golgi apparatus of plants by glycosyl transferases from mammals in order to "humanize" or "mammalize" the glycans of the glycoproteins they produce. The success of such a strategy is nonetheless not evident. In particular, the galactosylation and subsequent sialylation of recombinant glycoproteins in a vegetable cell depends not only on the transfer and the expression of the gene of the galactosyl and the sialyl transferase: these foreign enzymes must also be active in the vegetable cell, without detrimental effects to the plant cell, and last but not least, without detrimental effects to the transgenic plant as a whole.

To mammalise the glycosylation of plant for the production of tailor made glycoproteins in plants a xylosyltransferase and fucosyltransferase can be knocked out and at least one of several mammalian glycosyltransferases have to be expressed. Providing the xylosyltransferase and fucosyltransferase knock-outs and thereby reducing the unwanted glycosylation potential of plants is a feasible option because for example an *Arabidopsis thaliana* mutant mutated in the gene encoding N-acetylglucosaminyltransferase I was completely viable (Von Schaewen et al., 1993). As N-acetylglucosaminyltransferase I is the enzyme initiating the formation of complex glycans (Schachter, 1991), this plant completely lacks the xylose and fucose containing complex glycans.

In a preferred embodiment, the invention provides a plant comprising a functional (mammalian) protein, e.g. a transporter or an enzyme providing N-glycan biosynthesis that is normally not present in plants additionally comprising at least a second mammalian protein or functional fragment thereof that is normally not present in plants. It is provided by the invention to produce in plants a desired glycoprotein having a mammalian-type of glycosylation pattern, at least in that said glycoprotein is galactosylated. Again, desired glycoproteins may be any useful glycoprotein for which mammalian-like glycosylation is relevant.

In a preferred embodiment, the invention provides a plant according to the invention wherein said functional mammalian enzyme providing N-glycan biosynthesis that is normally not present in plants comprises (human) β1,4-galactosyltransferase. An important mammalian enzyme that is missing in plants is this β1,4-galactosyltransferase. cDNA's encoding this enzyme has been cloned from several mammalian species (Masri et al., 1988; Schaper et al., 1986). The enzyme transfers galactose from the activated sugar donor UDP-Gal in β1,4 linkage towards GlcNAc residues in N-linked and other glycans (FIG. 1). These galactose residues have been show to play an important role in the functionality of e.g. antibodies (Boyd et al., 1995). β1,4-galactosyltransferase has recently been introduced in insect cell cultures (Hollister et al., 1998; Jarvis and Finn, 1996) to extend the N-glycosylation pathway of Sf9 insect cells in cell culture, allowing infection of these cultures with a baculovirus expression vector comprising a nucleic acid encoding a heterologous protein. It was shown that the heterologous protein N-linked glycans were to some extent more extensively processed, allowing the production of galactosylated recombinant glycoproteins in said insect cell cultures. Also the introduction of the enzyme into a tobacco cell suspension culture resulted in the production of galactosylated N-liked glycans (Palacpac et al., 1999) of endogenous proteins. However, no heterologous glycoproteins were produced in these plant cell cultures, let alone that such heterologous proteins would indeed be galactosylated in cell culture. Furthermore, up to date no transgenic plants comprising mammalian glycosylation patterns have been disclosed in the art. Many glycosylation mutants exist in mammalian cell lines Stanley and Ioffe, 1995; Stanley et al., 1996). However, similar mutations in complete organisms cause more or less serious malfunctioning of this organism (Asamo et al., 1997; Herman and Hovitz, 1999; Loffe and Stanley, 1994). It is therefor in general even expected that β1,4-galactosyltransferase expression in a larger whole than cells alone (such as in a cohesive tissue or total organism) will also lead to such malfunctioning, for example during embryogenesis and/or organogenesis. Indeed, no reports have been made until now wherein a fully grown non-mammalian organism, such as an insect or a plant, is disclosed having the capacity to extend an N-linked glycan, at least not by the addition of a galactose. From many eukaryotic multicellular organisms, immortalized cell lines such as CHO, Sf9 and hybridoma cell lines have been generated. These cell lines have been cultured for many generations, can carry many mutations and lack or have lost many characteristics which are essential for functioning of the intact organisms from which they are derived. To illustrate the latter, the fact that these immortalized cell lines can not be regenerated into complete intact organisms shows that important signaling pathways and components involved in cell-cell communication are lacking in these immortalized cell lines. It is known from literature that the N-linked glycosylation machinery of immortalized eukaryotic cell lines, such as CHO cells (Stanley and Loffe, 1995; Stanley et al., 1996) or Sf insect cell lines (Jarvis and Finn, 1996; Hollister et al., 1998), can be modified without having obvious negative effects on the viability of these cell lines, whereas in contrast similar mutations in complete organisms cause more or less serious malfunctioning of the organism (Aseno et al., 1997; Herman and Horvitz, 1999; Loffe and Stanley, 1994). Indeed no reports have been made that N-linked glycosylation can be extended, in such a way that N-linked glycans are formed that naturally do not occur, in eukaryotic cells which do have the potency to regenerate into viable organisms. Apparently, as compared to normal cells, immortalized cell lines are flexible and tolerant to new, not normal types of N-linked glycosylation but lack the capacity to develop into intact organisms.

Also modification of the N glycosylation machinery of immortalized tobacco BY2 cells has been reported. Introduction of GalT into this cell line results in the production of galactosylated N-linked glycans of endogenous proteins Palacpac et al., 1999). However, cells from this BY2 cell line can not be regenerated into viable tobacco plants. In addition and as described elsewhere in this patent application, the largest population was an abnormal hybrid type glycan (GlcNAc2Man5GlcNAcGal) suggesting premature action of the introduced galactosyltransferase and an abnormal Golgi morphology and localisation of the galactosyltransferase in the BY2 cell line. This provides further evidence that this cell lines is significantly different from normal tobacco plant cells.

No reports have been made until now wherein a fully grown non-mammalian organism such as an insect or plant, is disclosed having the capacity to extend an N-linked glycan, at least not by the addition of a galactose.

Surprisingly, the invention now provides such a non-mammalian organism, a plant having been provided a (functional) mammalian enzyme providing N-glycan biosynthesis that is normally not present in plants thereby for example providing the capacity to extend an N-linked glycan by the addition of a galactose. In a preferred embodiment, the invention provides such a plant wherein said enzyme shows stable expression. It is even provided that beyond said second mammalian protein a third mammalian protein is expressed by a plant as provided by the invention. The experimental part provides such a plant that comprises a nucleic acid encoding both an antibody light and heavy chain or (functional) fragment thereof. Of course, it is not necessary that a full protein is expressed, the invention also provides a plant according to the invention expression only a fragment, preferably a functional fragment of said second mammalian glycoprotein, said fragment having at least one activity of the whole protein and further being characterised by for example a truncated polypeptide chain, or a not fully extended glycan, for example only extended with galactose.

Figure 5:
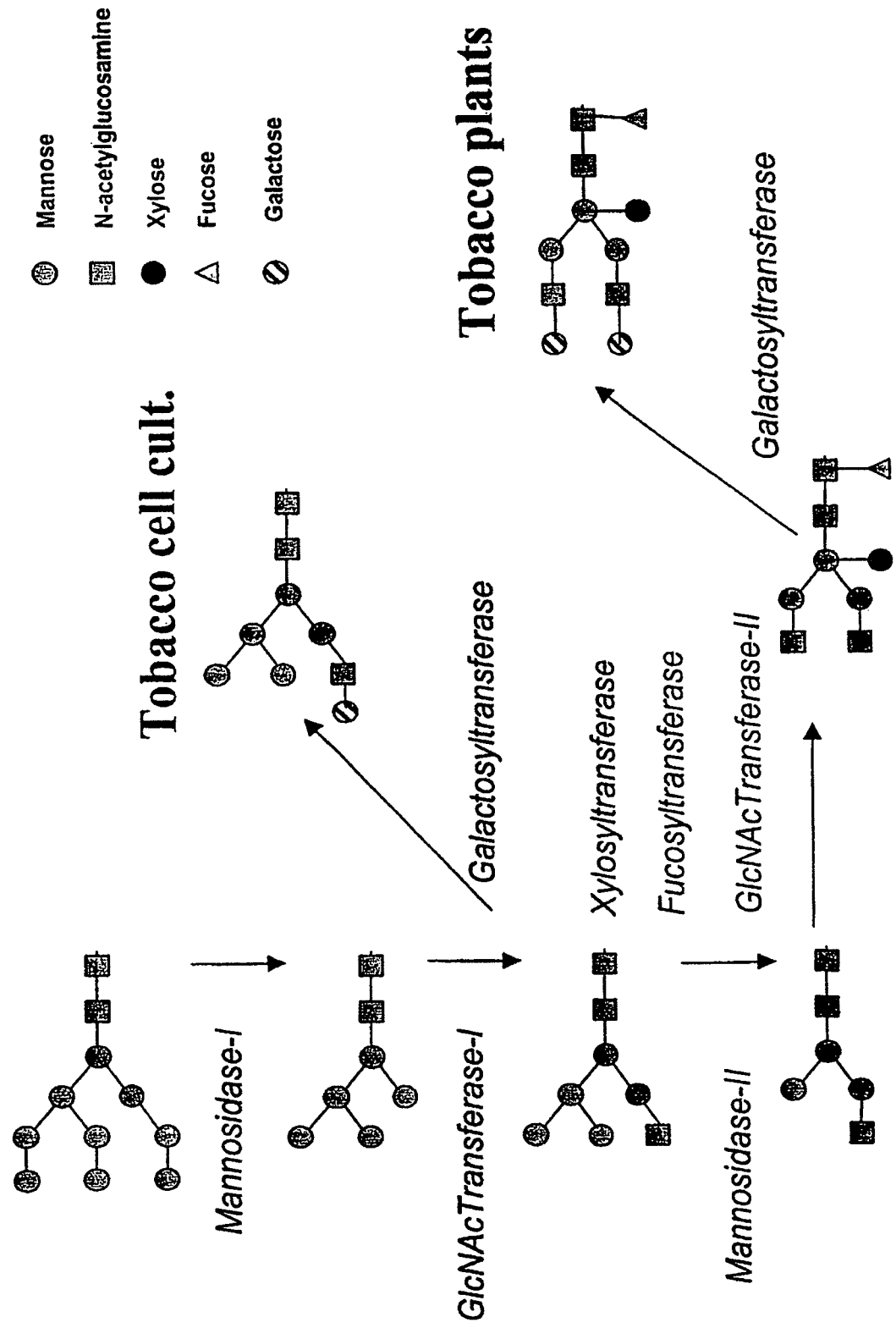

In a preferred embodiment, the invention provides a plant according to the invention wherein said second mammalian protein or functional fragment thereof comprises an extended N-linked glycan that is devoid of xylose and/or of fucose. As can be seen from FIG. 3, plant-derived galactosylated glycoproteins still may contain xylose and fucose residues. This in contrast to plant cell culture derived galactosylated glycoproteins (Palacpac et al., 1999) where these glycoproteins are essentially devoid of xylose and fucose residues. In plant cell cultures this is a result of the action of β1,4-galactosyltransferase on immature N-linked glycans, resulting in unnatural galactosylated 'hybrid type' N-linked glycans in which Golgi-mannosidase II and N-acetylglucosaminyltransferase II can not perform their function anymore. In a preferred embodiment, β1,4-galactosyltransferase is therefor expressed in plants in such a way that the enzyme acts in the Golgi'apparatus on the natural substrates (FIG. 5). This means, after the action of N-acetylglucosaminyltransferase I, Golgi-mannosidase II and N-acetylglucosaminyltransferase II (and in plants, provided that these enzymes are not inhibited in another way, after or during the action of xylosyltransferase and fucosyltransferase). The present invention provides an plant in which galactosylation is essentially natural like it occurs in mammals.

The N-terminal cytoplasmic, transmembrane and stem region of glycosyltransferases determine the localisation of the enzyme in the ER or Golgy membrane. To provide natural or desirable glycosylation, glycosyltransferases can be expressed in plants as they occur in mammals, but can also be expressed as a fusion protein between two, or part of two, different glycosyltransferases. In this case the localisation is determined by one enzyme and the catalytic activity by a second enzyme. As example, a fusion between the cytoplasmic, transmembrane and stem region of plant xylosyltransferase and the catalitic domain of mammalian galactosyltransferase, providing an enzyme with galactosyltransferase activity and localisation of the xylosyltransferase.

If one would desire to further separate glycoproteins comprising extended N-linked glycan that is devoid of xylose and/or of fucose, or to produce these in a more purified way, several possibilities are open. For one, several types of separation techniques exist, such as (immuno)affinity purification or size-exclusion chromatography or electrophoresis, to mediate the required purification. Furthermore, another option is to use as starting material plants wherein the genes responsible for xylose and/or fucose addition are knocked-out.

In another embodiment, the invention provides a plant according to the invention wherein said N-linked glycan comprising galactose is further comprising sialic acid added thereto. In particular, the transfer of genes coding for sialyl transferases, enzymes which catalyze the addition of sialic acid on the glycan, into vegetable systems leads to even more stable glycoproteins during in vivo usage and hence better adapted to a possible therapy. The invention herewith provides the transfer of a sialic acid biosynthesis pathway to plants. In this invention when referring to plants the whole spectrum of plants ranging from algae to trees is intended unless otherwise specified. Plants in general lack sialic acid, a sugar residue needed for the enhanced function of certain glycoproteins like antibodies and hormones, in their N-linked glycans and also the substrates for sialylation have never been found. The invention provides plants that, have the capacity to produce NeuAc containing N-linked glycans on their proteins. To establish this, up to 5 different heterologous genes are expressed in plants (see Table 1). To provide plants with the biosynthetic capacity to produce sialic acid, genes encoding up to five enzymes acting in the sialic acid biosynthesis pathway are transformed to plants. These enzymes from bacterial and mammalian origin are known: GlcNAc-2 epimerase, NeuAc synthase, CMP-NeuAc synthetase, CMP-NeuAc transporter and NeuAc transferase. All genes encoding the enzymes are if desired supplied with a (FLAG) tag to follow expression, and are transformed to e.g. tobacco and corn.

In another preferred embodiment, the invention provides a plant according to the invention wherein said N-linker glycan comprising galactose is further comprising or extended with glucoronic acid, glucoronyl, sulfate, sulfon, fucose, or other compound capable of extending galactose with linked to said galactose. This is particularly relevant since experiments have shown, that the absence of terminal sialic acid on glycosidic side chains can in general dramatically decrease biological activity in vivo. Most likely, asialo-glycoprotein-receptors in the liver can bind to asialo-glycoprotein, and thereby cause a clearance of the glycoprotein from the circulation, which is reflected in a reduced metabolic half life and low bioactivity in vivo. The presence of for example GlcA or another extending group but sialic acid has the same effect as the presence of sialic acid, it hinders the binding of a thus modified protein to the asialo-glycoprotein receptor of for example liver cells, thereby effectively increasing half-life, and thus clearance time, of such proteins, when used as therapeutic substance, i.e. as pharmaceutical composition. The invention thus provides an organism derived, herein in particular a plant-derived glycoprotein or functional fragment thereof comprising an extended N-linked glycan at least comprising galactose, said galactose further extended with a compound capable of extending galactose with, such as Glca to function in a similar way as silaic acid. For example, the invention provides plants that have the capacity to produce GlcA containing N-linked glycans on their proteins. To establish this, a gene encoding for example glucuronyltransferase (Terayama et al., PNAS 94:6093-6098, 1997) is expressed in plants according to the invention using methods known in the art or herein disclosed.

In this aspect, the invention is not limited to plants but also provides other organisms like animals, fungi or yeast, or cell lines like mammalian cell lines or insect cell lines with the capacity to produce a glycoprotein (essentially non-sialiated) according to the invention wherein said N-linked glycan comprising galactose is further comprising or extended with for example glucuronic acid linked to galactose; which in essence has the same effect as the presence of sialic acid. The invention is not limited to extending the galactose by glucuronic acid which has the essentially the same effect as the presence of sialic acid in that it increase biological half-life and clearance time. Also sulfate, fucose or any other compound can be linked to galactose, thereby extending the carbohydrate group, by expressing a sulfotransferase, fucosyltransferase or other enzyme that transfers sulfate, fucose or other compound to galactose residues can be used to increase half-life. The invention thus provides a method to increase half-life or improve clearance time of a pharmaceutical composition comprising as active component a glycoprotein, comprising providing said glycoprotein with a compound, attached to galactose, that replaces or provides sialic acid function and thus provides at least reduced reactivity with a asialo-glycoprotein-receptor, preferably wherein said receptor is at least present on a liver-cell. Also more than one compound can be transferred to galactose, for example glucuronic acid that is extended by sulfate by expressing a sulfotransferase that transfers sulfate to glucuronic acid. The invention is not limited to those cases in which extension of galactose by other compounds than sialic acid has the same effect as extension with sialic acid. Extension of galactose by other compounds than sialic acid can have a function by its own for example in interaction with other compounds, cells or organisms.

Figure 6:
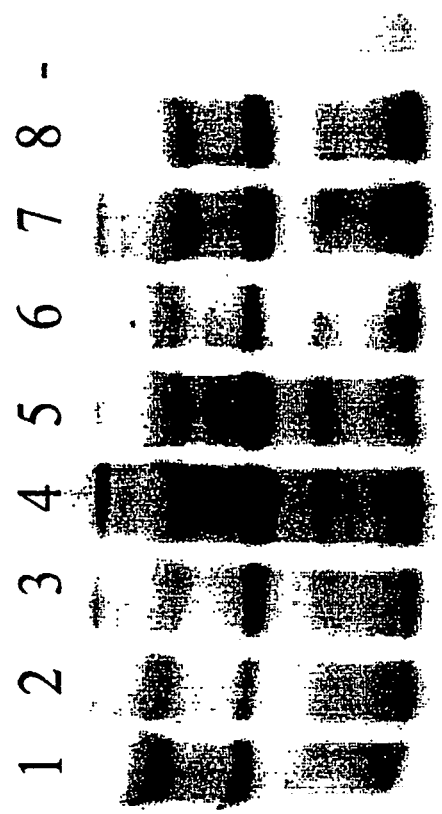

Furthermore, it has the advantage that components, otherwise extended by sialic acid, but now for example with glucoronic acid, or sulfate of fucose groups, for that matter, can easily be recognised and thus distinguished from like endogenous compounds extended with sialic acid. For example, a pharmaceutical composition comprising a glycosylated protein, such as a glycoprotein hormone, or erytrhopoetin (EPO), normally provided with sialic acid, but now with for example a sulfon, or with glucoronic acid, can easily be recognised, facilitating detection of the foreign compounds. As an example, FIG. 6 shows that tobacco plants that express human β1,4 galactosyltransferase and rat β1,3 glucuronyltransferase form the desired structure GlcAβ1,Gal on their glycoproteins as is clearly shown by the binding of a specific antibody (mouse monoclonal antibody 412) to GlcAβ1,Gal structure.

Extending galactose with other compounds than silalic acid can also have advantages for the production of recombinant proteins in plants. It can make the glycoprotein or glycan of the glycoprotein more stable by preventing galactosydases and/or other glycosydases from degrading the N-glycan. It can, by doing that, increase the galactosylation. It can also be of use in a purification procedure, for example by facilitating affinity purification by specific antibodies, lectins or other compounds. if desired, the compound by which galactose is extended or further comprised can, after purification of the recombinant glycoprotein, be removed, by for example a specific glycosydase, sulfatase, phosphatase, or other suitable enzyme.

In another preferred embodiment, the invention provides a plant according to the invention wherein said N-linked glycan comprising galactose is further comprising other sugar residues not directly linked to galactose, for example core alpha1,6 linked fucose or beta1,4- or beta1,6 linked N-acetylglucosamine (GlcNAc). To establish this, a gene or genes encoding for example core alpha1,6 fucosyltransferase or/and GlcNAc-transferase III, GlcNAc-transferase IV, GlcNAc-transferase V and/or GlcNAc-transferase VI are expressed in plants according to the invention using methods known in the art or herein disclosed.

In general, herein is provided a method to tailor N-linked glycosylation for the production of heterologous glycoproteins in plant species with typical plant like glycosylation patterns similar to those as shown in FIG. 1, i.e. which lack the typical mammalian proteins involved in N-linked glycosylation such as, but not limited to, beta1-4 galactosyltransferases and glucoronyl transferases.

Generating stably transformed plants which produce tailored glycoproteins with commercial interest can be established by inoculating plant cells or tissues with *Agrobacterium* strains containing a (binary) vector which comprises both nucleotide sequences encoding N-glycosylation modifying enzymes and genes encoding commercially interesting heterologous glycoproteins. Alternatively, stably transformed plants which produce tailored glycoproteins with commercial interest can be generated by simultaneous inoculation (co-transformation) of two or more *Agrobacterium* strains each carrying a vector comprising either nucleotide sequences encoding N-glycosylation modifying enzymes or nucleotide sequences encoding glycoproteins of commercial interest. Alternatively, stably transformed plants which produce tailored glycoproteins with commercial interest can be generated by (multiple) crossing(s) of plants with modified N-glycosylation with plants which express nucleotide sequences encoding proteins of commercial interest. In all of these procedures, the vector may also comprise a nucleotide sequence which confers resistance against a selection agent. In order to obtain satisfactorily expression of the proteins involved in N-glycosylation and of the glycoproteins or polypeptides of commercial interest, the nucleotide sequences may be adapted to the specific transcription and translation machinery of the host plant as known to people skilled in the art. For example, silent mutations in the coding regions may be introduced to improve codon usage and specific promoters may be used to drive expression of the said genes in the relevant plant tissues. Promoters which are developmentally regulated or which can be induced at will, may be used to ensure expression at the appropriate time, for example, only after plant tissues have been harvested from the field and brought into controlled conditions. In all these cases, choice of expression cassettes of the glycosylation modifying proteins and of the glycoproteins of commercial interest should be such that they express in the same cells to allow desired post translational modifications to the said glycoprotein.

In the detailed description the invention provides a plant as defined herein before according to the invention which comprises a tobacco plant, or at least a plant related to the genus *Nicotiana*, however, use for the invention of other relatively easy transformable plants, such as *Arabidopsis thaliana*, or *Zea mays*, or plants related thereto, is also particularly provided. For the production of recombinant glycoproteins, use of duckweed offers specific advantages. The plants are in general small and reproduce asexually through vegetative budding. Nevertheless, most duckweed species have all the tissues and organs of much larger plants including roots, stems, flowers, seeds and fronds. Duckweed can be grown cheaply and very fast as a free floating plant on the surface of simple liquid solutions from which they can easily be harvested. They can also be grown on nutrient-rich waste water, producing valuable products while simultaneously cleaning wastewater for reuse. Particularly relevant for pharmaceutical applications, duckweed can be grown indoors under contained and controlled conditions. Stably transformed Duckweed can for example be regenerated from tissues or cells after (co)-inoculating with *Agrobacterium* strains containing each a (binary) vector which comprises one or more nucleotide sequences of interest encoding N-glycosylation modifying enzymes and/or genes encoding commercially interesting heterologous glycoproteins. The duckweed plant may for example comprise the genus *Spirodella*, genus *Wolffia*, genus *Woiffiella*, or the genus *Lemna, Lemna minor, Lemna miniscula* and *Lemna gibba*.

Expression in tomato fruits also offers specific advantages. Tomatoes can be easily grown in greenhouses under contained and controlled conditions and tomato fruit biomass can be harvested continuously throughout the year in enormous quantities. The watery fraction containing the glycoproteins of interest can be readily separated from the rest of the tomato fruit which allows easier purification of the glycoprotein. Expression in storage organs of other crops including but not limited to the kernels of corn, the tubers of potato and the seeds of rape seed or sunflower are also attractive alternatives which provide huge biomass in organs for which harvesting and processing technology is in place.

Herewith, the invention provides a method for providing a transgenic plant, such as transgenic *Nicotiana, Arabidopsis thaliana*, or corn, potato, tomato, or duckweed, which are capable of expressing a recombinant protein; with the additional desired capacity to extend an N-linked glycan with galactose comprising crossing said transgenic plant with a plant according to the invention comprising at least one functional mammalian protein, e.g. a transporter or an enzyme providing N-glycan biosynthesis that is normally not present in plants, harvesting progeny from said crossing and selecting a desired progeny plant expressing said recombinant protein and expressing a functional (mammalian) enzyme involved in mammalian-like N-glycan biosynthesis that is normally not present in plants. In a preferred embodiment, the invention provides a method according to the invention further comprising selecting a desired progeny plant expressing said recombinant protein comprising an extended N-linked glycan et least comprising galactose. In the detailed description a further description of a method according to the invention is given using tobacco plants and crossings thereof as an example.

With said method as provided by the invention, the invention also provides a plant expressing said recombinant protein and expressing a functional (mammalian) enzyme involved in mammalian-like N-glycan biosynthesis that is normally not present in plants. Now that such a plant is provided, the invention also provides use of a transgenic plant to produce a desired glycoprotein or functional fragment thereof, in particular wherein said glycoprotein or functional fragment thereof comprises an extended N-linked glycan et least comprising galactose.

The invention additionally provides a method for obtaining a desired glycoprotein or functional fragment thereof comprising for example an extended N-linked glycan at least comprising galactose comprising cultivating a plant according to the invention until said plant has reached a harvestable stage, for example when sufficient biomass has grown to allow profitable harvesting, followed by harvesting said plant with established techniques known in the art and fractionating said plant with established techniques known in the art to obtain fractionated plant material and at least partly isolating said glycoprotein from said fractionated plant material. In the detailed description (see for example FIG. 4) is further explained that an antibody having been provided with an extended N-linked glycan at least comprising galactose is provided.

The invention thus provides a plant-derived glycoprotein or functional fragment thereof comprising an extended N-linked glycan at least comprising galactose, for example obtained by a method as explained above. Such a plant-derived glycoprotein with an extended glycan at least comprising galactose essentially can be any desired glycoprotein that can be expressed in a plant. For example, antibodies, FSH, TSH and other hormone glycoproteins, other hormones like EPO, enzymes like antitrypsine or lipase, cellular adhesion molecules like NCAM or collagen can be produced in plants and be provided with essentially mammalian glycosylation patterns. Expression of such proteins can be performed by using a method known in the art. For example, by stable expression via *Agrobacterium* mediated transformation, electroporation or particle bombardment, but also by transient expression using a virus vector like PVX or other method, glycosyltransferases or an other protein extending glycan biosynthesis, and/or said glycoprotein could be expressed under control of a specific promoter to facilitate expression in certain tissues or organs.

Herewith, the invention also provides use of such a plant-derived glycoprotein or functional fragment thereof according to the invention for the production of a pharmaceutical composition, for example for the treatment of a patient with an antibody, a hormone, a vaccine antigen, an enzyme, or the like. Such a pharmaceutical composition comprising a glycoprotein or functional fragment thereof is now also provided. The invention is further explained in the detailed description without limiting it thereto.

DETAILED DESCRIPTION

One important enzyme involved in mammalian N-glycan biosynthesis that is not present in plants is $\beta$1,4-galactosyltransferase. Here, for one, the stable expression of $\beta$1, 4-galactosyltransferase in tobacco plants is described. The physiology of these plants is not obviously changed by introducing $\beta$1,4-galactosyltransferase and the feature is inheritable. Crossings of a tobacco plant expressing $\beta$1,4-galactosyltransferase with a plant expressing the heavy and light chain of a mouse antibody produced antibody having terminal galactose in similar amounts as hybridoma produced antibodies. Herein it is thus shown that the foreign enzyme can be successfully introduced in plants. A clear increase in galactose containing glycoproteins is observed. Moreover, this feature is inheritable and there is no visible phenotypical difference between the galactosyltransferase plants and wild type. A mouse monoclonal antibody produced in these plants has a degree of terminal galactoses comparable to hybridoma produced antibody. This shows that not only endogenous proteins become galactosylated but also a recombinantly expressed mammalian protein.

Materials and Methods

Plasmids and Plant Transformation

A plant transformation vector containing human $\beta$1,4-galactosyltransferase was constructed as follows: a 1.4 kb BamHI/XbaI fragment of pcDNAI-GalT (Aoki et al., 1992; Yamaguchi and Fukuda, 1995) was ligated in the corresponding sites of pUC19. Subsequently, this fragment was re-isolated using surrounding KpnI and HincII sites and cloned into the KpnI and SmaI site of pRAP33 (named pRAP33-HgalT). Using AscI and PacI sites the CaMV35S promotor-cDNA-Nos terminator cassette of pRAP33-HgalT was cloned in the binary vector pBINPLUS (van Engelen et al., 1995). Modifications to the published protocol are: After incubation with A. tum., leaf discs were incubated for three days in medium containing 1 mg/ml of NAA and 0.2 mg/ml BAP and the use of 0.25 mg/ml cefotaxime and vancomycine to inhibit bacterial growth in the callus and shoot inducing medium. 25 rooted shoots were transformed from in vitro medium to soil and, after several weeks, leaf material of these plants was analysed.

Northern Blotting

The $\beta$1,4-galactosyltransferase RNA level in the transgenic plants was analyzed by northern blotting (Sambrook et al., 1989) RNA was isolated from leafs of transgenic and control plants as described (De Vries et al., 1991). Ten µg of total RNA was used per sample. The blot was probed with a [$^{32}$P]dATP labeled SstI/XhoI fragment, containing the whole GalT cDNA, isolated from pBINPLUS-HgalT.

Glycoprotein Analysis

Total protein extracts of tobacco were prepared by grinding leafs in liquid nitrogen. Ground material was diluted 10 times in SDS page loading buffer (20 mM of This-HCl pH 6.8, 6% glycerol, 0.4% SDS, 20 mM DTT, 2.5 ig/ml Bromophenol Blue). After incubation at 100° C. for 5 min insoluble material was pelleted. Supernatants (12.5 µl/sample) were run on 10% SDS-PAGE and blotted to nitrocellulose. Blots were blocked overnight in 0.5% Tween-20 in TBS and incubated for 2 hours with peroxidase conjugated RCA$_{120}$ (Ricinus Communis Agglutinin, Sigma) (1 µg/ml) in TBS-0.1% tween-20. Blots were washed 4 times 10 minutes in TBS-0.1% tween-20 and incubated with Lumi-Light western blotting substrate (Roche) and analysed in a lumianalyst (Roche). A rabbit polyclonal antibody directed against Horseradish peroxidase (HRP, Rockland Immunochemicals) was split in reactivity against the xylose and fucose of complex plant glycans by affinity chromatography with bee venom phospholipase according to (Faye et al., 1993). A rabbit anti LewisA antibody was prepared as described (Fitchette Laine et al., 1997). Blots were blocked with 2% milkpowder in TBS and incubated in the same buffer with anti-HRP, anti-xylose, anti-fucose or anti-Lewis-A. As secondary antibody alkaline HRP-conjugated sheep-anti-mouse was used and detection was as described above.

Plant Crossings

Mgr48 (Smant et al., 1997) is a mouse monoclonal IgG that has been expressed in Tobacco plants. The construct used for transformation was identical to monoclonal antibody 21C5 expressed in tobacco (van Engelen et al., 1994). Flowers of selected tobacco plants with high expression of β1,4-galactosyltransferase were pollinated with plants expressing Mgr48 antibody. The F1 generation was seeded and plants were screened for leaf expression of antibody by western blots probed HRP-conjugated sheep-anti-mouse and for galactosyltransferase expression by RCA as described above.

Purification of IgG1 from Tobacco

Freshly harvested tobacco leaves were ground in liquid nitrogen. To 50 g of powdered plant material, 250 ml of PBS, containing 10 mM Na$_2$S$_2$O$_5$, 0.5 mM EDTA, 0.5 mM PMSF and 5 g polyvinylpolypyrrolid, was added. After soaking for 1 hour (rotating at 4° C.), insoluble material was removed by centrifugation (15 min, 15,000 g, 4° C.). The supernatant was incubated overnight (rotating at 4° C.) with 1 ml of proteinG-agarose beads. The beads were collected in a column and washed with 10 volumes of PBS. Bound protein was eluted with 0.1 M glycine pH 2.7 and immediately brought to neutral pH by mixing with 1 M Tris pH 9.0 (50 µl per ml of eluate). Purified antibody was quantified by comparison of the binding of HRP-conjugated sheep-anti-mouse to the heavy chain on a western blot with Mgr48 of known concentration purified from hybridoma medium (Smant et al., 1997).

Hybridoma Mgr48 and plant produced Mgr48 was run on 10% SDS-PAGE and blotted as described above. Detection with RCA was as described above. For antibody detection, blots were probed with HRP-conjugated sheep-anti-mouse and detected with Lumi-Light western blotting substrate as described above.

Results

Human β1,4-Galactosyltransferase Galactosylates Endogenous Proteins in *Nicotiana tobacum*.

Human β1,4-galactosyltransferase (Masri et al., 1988) was introduced in tobacco plants by *Agrobacterium* mediated leaf disk transformation of plasmid pBINPLUS-HgalT containing a cDNA that includes a complete coding sequence. Twenty-five plants selected for kanamicin resistance were analysed for mRNA levels by northern hybridization (FIG. 2A). The same plants were analyzed by the galactose binding lectin RCA$_{120}$ (Ricinus Cummunis Agglutinin). RCA binds to the reaction product of β1,4-GalT (Galβ1,4GlcNAc) but also to other terminal β linked galactose residues. RCA binds to one or more high molecular weight proteins isolated from non transgenic control tobacco plants (FIG. 2B). Probably these are Arabinogalactan or similar proteins. RCA is known to bind to Arabinogalactan proteins (Schindler et al., 1995). In a number of the plant transformed with Human β1,4-galactosyltransferase, in addition, binding of RCA to a smear of proteins is observed. This indicates that in these plants many proteins contain terminal β linked galactose residues. There is a good correlation between the galactosyltransferase RNA expression level and the RCA reactivity of the trangenic plants. Human β1,4-galactosyltransferase expressed in transgenic plants is therefor able to galactosylate endogenous glycoproteins in tobacco plants.

Figure 3:
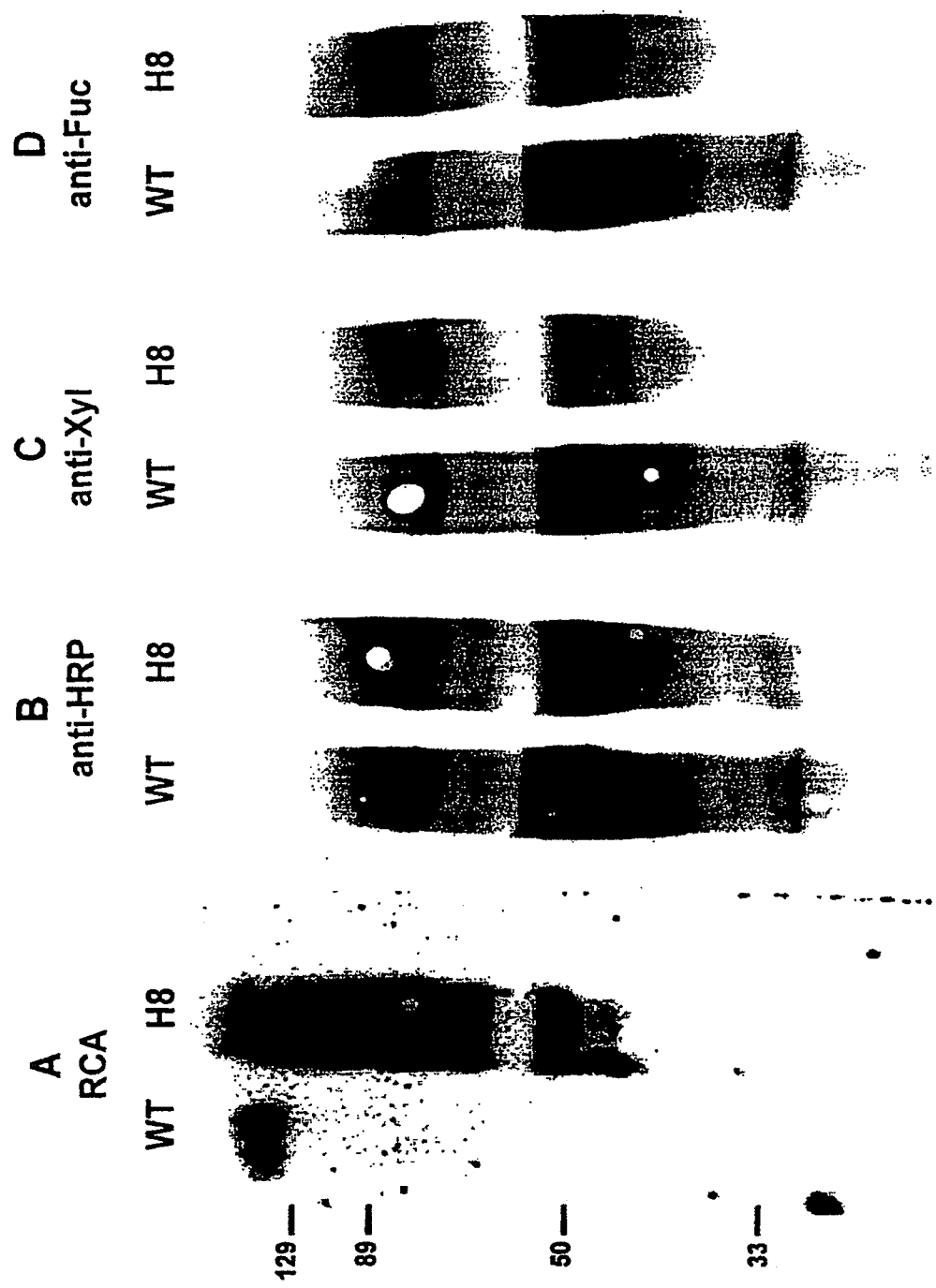

As it is known that galactosylated N-glycans are poor Acceptors for plant xylosyl- and fucosyltransferase (Johnson and Chrispeels, 1987), the influence of expression of β1,4-galactosyltransferase on the occurrence of the xylose and fucose epitope was investigated by specific antibodies. A polyclonal rabbit anti-HRP antibody that reacts with both the xylose and fucose epitope shows a clear difference in binding to isolated protein from both control and transgenic plants (FIG. 3).

Recombinantly Produced Antibody is Efficiently Galactosylated.

The effect of expression of β1,4-galactosyltransferase on a recombinantly expressed protein was investigated. Three tobacco plants expressing β1,4-galactosyltransferase (no. GalT6, GalT8 and GalT15 from FIG. 2) were selected to cross with a tobacco plant expressing a mouse monoclonal antibody. This plant, expressing monoclonal mgr48 (Smant et al., 1997), was previously generated in our laboratory. Flowers of the three plants were pollinated with mgr48. Of the F1 generation 12 progeny plants of each crossing were analysed for the expression of both antibody and β1,4-galactosyltransferase by the method described in materials and methods. Of crossing GalT6×mgr48 and GalT15×mgr48 no plants were found with both mgr48 and GalT expression. Several were found in crossing GalT8×mgr48. Two of these plants (no. 11 and 12), were selected for further analysis.

Figure 4:
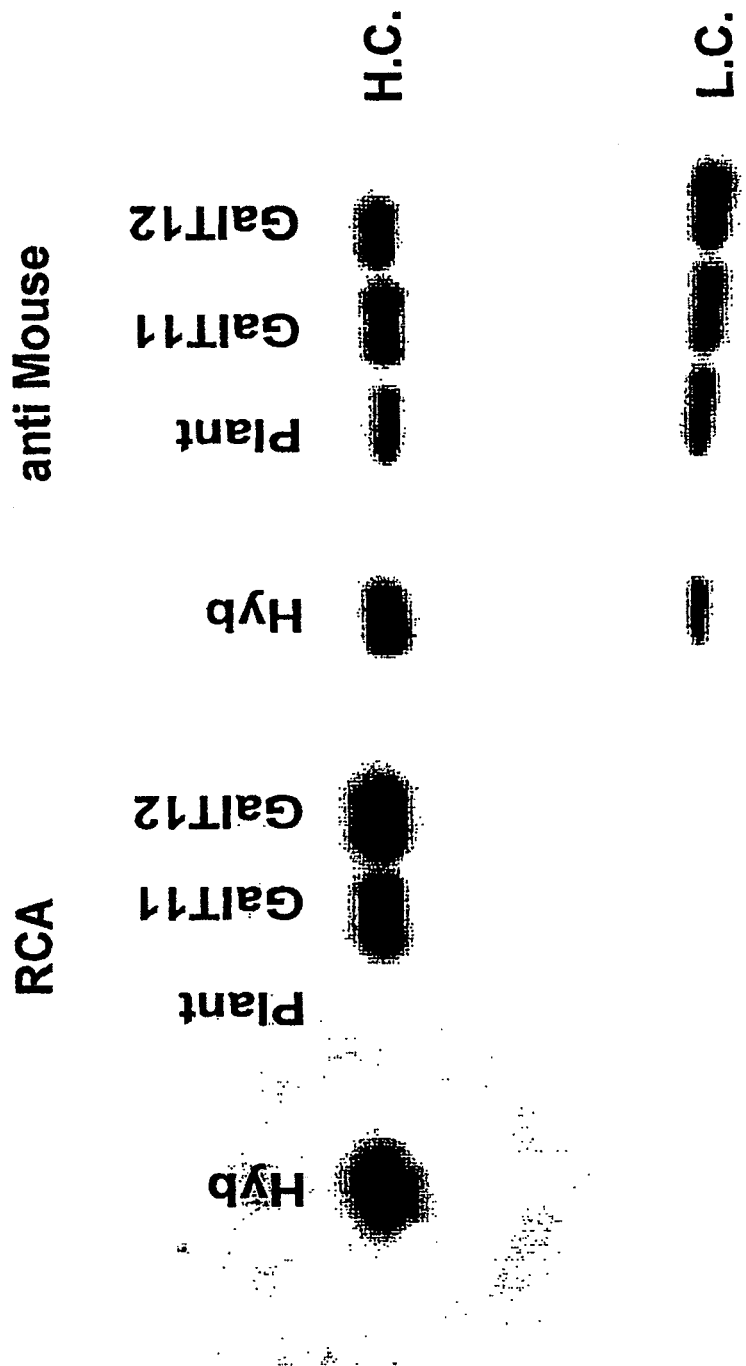

Using proteinG affinity, antibody was isolated from tobacco plants expressing mgr48 and from the two selected plants expressing both mgr48 and β1,4-galactosyltransferase. Equal amounts of isolated antibody was run on a protein gel and blotted. The binding of sheep-anti-mouse-IgG and RCA to mgr48 from hybridoma cells, tobacco and crossings GalT8×mgr48-11 and 12 was compared (FIG. 4). Sheep-anti-mouse-IgG bound to both heavy and light chain of all four antibodies isolated. RCA, in contrast, bound to hybridoma and GalT plant produced antibody but not to the antibody produced in plants expressing only mgr48. When the binding of sheep-anti-mouse-IgG and RCA to the heavy chain of the antibody is quantified, the relative reaction of RCA (RCA binding/sheep-anti-mouse-IgG binding) to GalT8×mgr48-11 and 12 is respectively 1.27 and 1.63 times higher than the ratio of hybridoma produced antibody. This shows that RCA binding to the glycans of antibody produced in GalT plants is even higher than to hybridoma produced antibody. Although the galactosylation mgr48 from hybridoma is not quantified, this is a strong indication that the galactosylation of antibody produced in these plants is very efficient.

Construction of Plant Expression Vectors with cDNA's Encoding α2,6 Sialyltransferase, β1,3-Glucuronyltransferase and β1,4-Galactosyltransferase.

The available β1,4-galactosyltransferase vector was not in a suitable format to easily combine with α2,6-sialyltransferase and β1,3-glucuronyltransferase clones. Therefore, by using PCR, the coding region of β1,4-galactosyl-transferase cDNA, α2,6-sialyltransferase cDNA and β 1,3-glucuronyltransferase cDNA have been cloned in plant expression vectors. Constructs are made in which galactosyltransferase is combined with either sialyltransferase or glucuronyltransferase in one vector, in order to enable simultaneous expression of the enzymes in transgenic plants after only one transformation. The galactosyltransferase expression is controlled by the 35S promoter, whereas expression of sialyltransferase and glucuronyltransferase is controlled by the 2' promoter.

There is a need for an accessible and standardised source of FSH for therapeutic and diagnostic purposes, which is guaranteed to be free of LH activity.

FSH preparations normally are derived from ovine or porcine pituitaries, which always implies the presence of (traces of) LH, and the risk of contamination with prion-like proteins. Substitution of brain derived FSH for plant produced recombinant FSH may be a good method of eliminating these problems. However, production of bioactive animal glycoproteins in plants, especially for therapeutic purposes, requires modification of plant-specific sugar sidechains into a mammalian type of glycans. The invention provides recombinant bFSH by infecting stably transformed tobaccoplants capable of forming mammalian type of glycans, with recombinant Tobacco Mosaic Virus TMV containing the genes for bFSH or bFSHR.

Construction of Single Chain (sc) bFSH into pKS (+) Bluescript Vector, Construction of sc-bFSH-TMV and sc-bFSH-HIS-TMV In order to circumvent the need of simultaneous expression of the two separate genes of bFSH-alpha and bFSH-beta subunits in plants, we decided to construct a bFSH fusion gene.

By overlap PCR we fused the carboxyl end of the beta subunit to the amino end of the alpha subunit (without a linker). In addition, we constructed a second sc-bFSH version carrying a 6×HIS tag at the C-terminus of the alpha subunit, which will allow us to purify the recombinant protein from the plant. Both, sc-bFSH and sc-bFSH-HIS constructs were subcloned into the cloning vector pKS(+) bluescript. The correctness of the clones was confirmed by sequence analysis.

Sc-bFSH was subcloned into the TMV vector. Two positive clones were chosen to make in vitro transcripts and Inoculate N. Bentahamiana plants. After a few days, plants showed typical viral infection symptoms, which suggested the infective capacity of the recombinant TMV clones. In order to test whether the sc-bFSH RNA is stably expressed in systemically infected leaves, 8 days post inoculation RNA was isolated from infected N. benthamiana leaves and a reverse transcriptase polymerase chain reactions using bFSH specific primers was performed. In all cases we obtained a PCR fragment of the expected size, indicating the stability of our Sc-bFSH-TMV construct. Extracts of infected plants are used for Western blot analyses and ELISA to determine whether Sc-bFSH is expressed and folded properly.

Abbreviations Used:
GlcNAc, N-Acetylglucosamine; Fuc, fucose; Gal, galactose; GalT, â1,4-galactosyltransferase; RCA, Ricinus Cummunis Agglutinin; Tables
Tables

TABLE 1

Enzymes of sialic acid biosynthesis pathway

| No | enzyme | Catalysed reaction | localisation | origin |
|---|---|---|---|---|
| 1 | GlcNAc-2 epimerase | GlcNAc ←→ ManNAc | cytoplasm | pig |
| 2 | NeuAc synthase | ManNAc + PEP ←→ NeuAc | cytoplasm | *Clostridium* |
| 3 | CMP-NeuAc synthetase | NeuAc + CMP → CMP-NeuAc | nucleus | mouse |
| 4 | CMP-NeuAc transporter | Cytoplasm → Golgi lumen | Golgi membrane | mouse |
| 5 | NeuAc transferase | CMP-NeuAc + Gal-R → NeuAc-Gal-R + CMP | Golgi | human |
| | Gal transferase | UDP-Gal + GlcNac-R → Gal-GlcNAc-R + UDP | Golgi | human |

Figure Legends

FIG. 1

Major differences between mammalian and plant complex N-linked glycans. Drawn are typical N-linked glycans. Numerous variations, both extended or truncated, occur in mammals and plants.

FIG. 2

Comparison of RNA levels and product of β1,4-galactosyltransferase. Upper panel: Northern blot of total RNA isolated from 25 transgenic plants, including a not transformed control plant (0), detected with a human β1,4-galactosyltransferase probe. Lower panel: Western blot of the same plant probed with RCA to detect terminal galactose residues on glycoproteins. M. indicates the molecular weight marker.

FIG. 3

Figure 2:
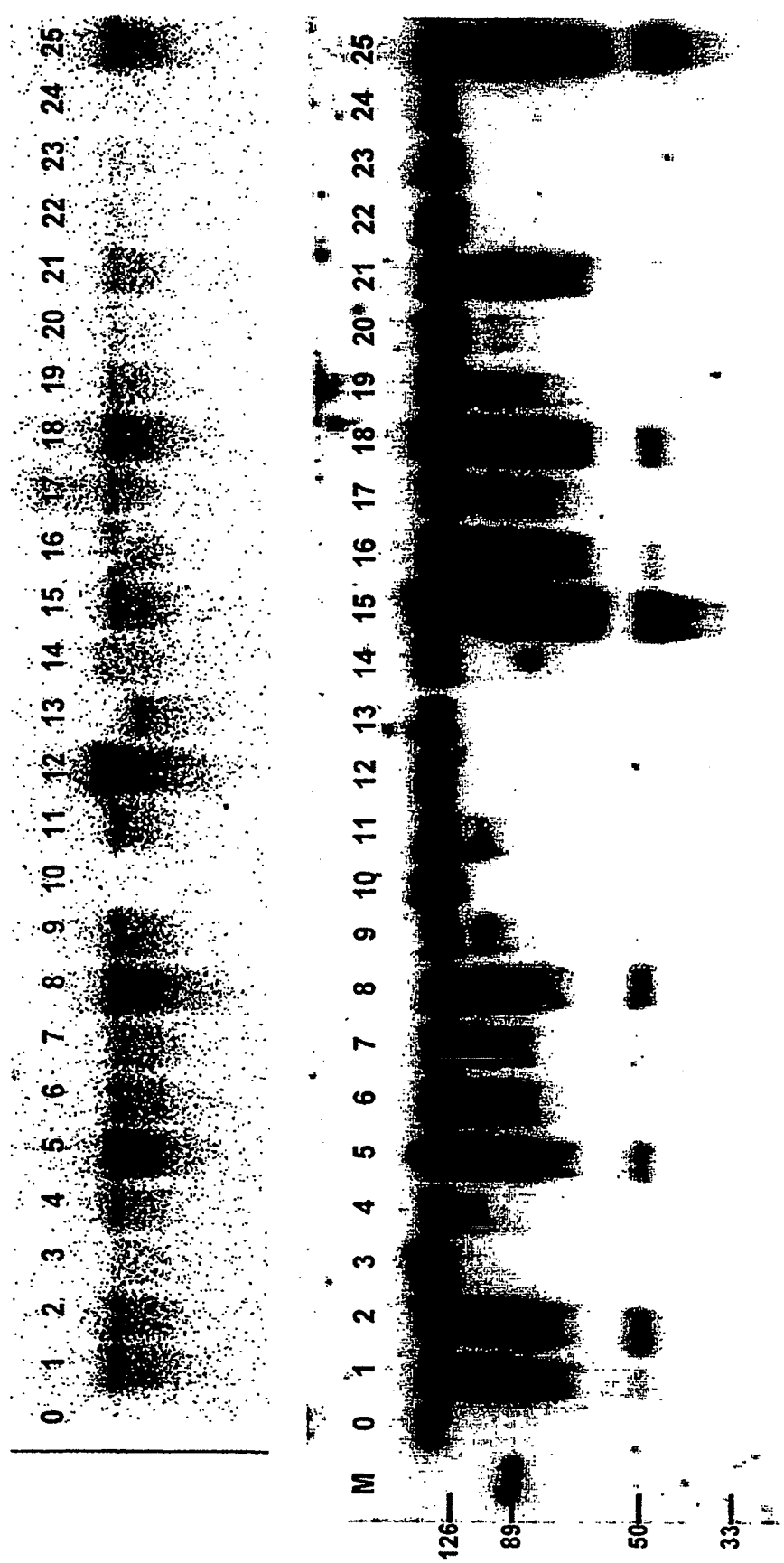

Western blot showing the binding of lectin and antibody to protein isolated from wild-type and a β1,4-galactosyltransferase plant (no. 8 from FIG. 2). A: RCA as in FIG. 2, B: anti HRP (detecting both xylose and fucose) antibody, C: anti xylose antibody, D: anti fucose antibody.)

FIG. 4

Western blot showing RCA and sheep-anti-mouse-IgG binding to purified antibody produced in hybridoma culture (Hyb), tobacco plants (plant) and tobacco plants co-expressing β1,4-galactosyltransferase (GalT11 and GalT12). H.C.: heavy chain, L.C. light chain.

FIG. 5

Tobacco cell cultures expressing galactosyltransferase produce unnatural hybrid N-glycans while tobacco plants expressing galactosyltransferase have natural, mammalian like galactosylation. To get natural galactosylation, galactosyltransferase should act after mannosidase II and GlcNAc-Transferase II.

FIG. 6

Western blot showing the expression of GlcAβ1,3Gal structure in transgenic tobacco by binding of an antibody (412) directed against the glucuronic acid-galactose (GlcAβ1,3Gal) structure to protein isolated from 8 plants expressing human β1,4 galactosyltransferase and rat β1,3 glucuronyltransferase and a wildtype control plant (−).

References

Aoki, D., Lee, N., Yamaguchi, N., Dubois, C., and Fukuda, M. N. (1992). Golgi retention of a trans-Golgi membrane protein, galactosyltransferase, requires cysteine and histidine residues within the membrane-anchoring domain. Proceedings Of The National Academy Of Sciences Of The United States Of America 89, 4319-4323.

Asano, M., Furukawa, K., Kido, M., Matsumoto, S., Umesaki, Y., Kochibe, N., and Iwakura, Y. (1997). Growth retardation and early death of beta-1,4-galactosyltransferase knockout mice with augmented proliferation and abnormal differentiation of epithelial cells. Embo j 16, 1850-7.

Boyd, P. N., Lines A. C., and Patel A. K. (1995). The effect of the removal of sialic acid, galactose and total carbohydrate on the functional activity of Campath-1H. Mol immunol 32, 1311-8.

Cabanes Macheteau, M., Fichette Laine, A. C., Loutelier Bourhis, C., Lange, C., Vine, N. D., Ma, J. K., Lerouge, P., and Faye, L. (1999). N-Glycosylation of a mouse IgG expressed in transgenic tobacco plants. Glycobiology 9, 365-72.

De Vries, S., Hoge, H., and Bisseling, T. (1991). Isolation of total and polysomal RNA from plant tissues. In Plant Molecular Biology Manual, B. Gelvin, R. A. Schilperoort and D. P. S. Verma, eds. (Dordrecht: Kluwer Academic Publishers), pp. B6/1-13.

Dieryck, W., Pagnier J., Poyart, C., Marden, M. C., Gruber, V., Bournat, P., Baudino, S., and Merot, B. (1997). Human haemoglobin from transgenic tobacco [letter] Nature 386, 29-30.

Faye, L., Gomord, V., Fitchette Laine, A. C. and Chrispeels, M. J. (1993). Affinity purification of antibodies specific for Asn-linked glycans containing alpha 1-→3 fucose or beta 1-→2 xylose. Anal Biochem 209, 104-8.

Fichette Laine, A. C., Gomord, V., Cabanes, M., Michalski, J. C., Saint Macary, M., Foucher, B., Cavelier, B., Hawes, C., Lerouge, P., and Faye, L. (1997). N-glycans harboring the Lewis a epitope are expressed at the surface of plant cells. Plant J 12, 1411-7.

Florack, D., Allefs, S., Bollen, R., Bosch, D., Visser, B., and Stiekema, W. (1995). Expression of giant silkmoth cecropin B genes in tobacco. Transgenic Research 4, 132-141.

Herman, T., and Horvitz, H. R. (1999). Three proteins involved in *Caenorhabditis elegans* vulval invagination are similar to components of a glycosylation pathway. Proc Natl Acid Sci USA 96, 979-9.

Hollister, J. R., Shaper, J. H. and Jarvis, D. L. (1998). Stable expression of mammalian beta, 1,4-galactosyltransferase extends the N-glycosylation pathway in insect cells. Glycobiology 8, 473-80.

Horsch, R. B., Fry, J. E., Hoffmann, N. L., Eichholtz, D., Rogers, S. G., and Fraley, R. T. (1985). A simple and general method for transferring genes into plants. Science, USA 227, 1229-1231.

Ioffe, E., and Stanley, P. (1994). Mice lacking N-acetylglucosaminyltransferase I activity die at mid-gestation, revealing and essential role for complex or hybrid N-linked carbohydrates. Proc Natl Acid Sci USA 91, 728-32.

Jarvis, D. L., and Finn, E. E. (1996). Modifying the insect cell N-glycosylation pathway with immediate early baculovirus expression vectors. Nat Biotechnol 14, 1288-92.

Jenkins, N. Parekh, R. B., and James D. C. (1996). Getting the glycosylation right: implications for the biotechnology industry. Nat Biotechnol 14, 975-81.

Johnson, K. D., and Chrispeels, M. J. (1987). Substrate specificities of N-acetylglucosaminyl-, fucosyl-, and xylosyl-transferases that modify glycoproteins in the Golgi apparatus of bean cotyledons. Plant Physiology 84, 1301-1308.

Lerouge, P., Cabanes Macheteau, M., Rayon, C, Fischette Laine, A. C., Gomord, V, and Faye, L. (1998). N-glycoprotein biosynthesis in plants: recent developments and future trends. Plant Mol Biol 38, 31-48.

Ma, J. K., Hiatt, A., Hein, M., Vine, N. D., Wang, F., Stabila, P., van Dolleweerd, C., Mostov, K. and Lehner, T. (1995). Generation And assembly of secretory antibodies in plants [see comments.] Science 268, 716-9.

Masri, K. A., Appert, H. E., and Fukuda, M. N. (1988). Identification of the full-length coding sequence for human galactosyltransferase (beta-N-acetylglucosaminide: beta 1,4-galactosyltransferase). Biochem Biophys Res Commun 157, 657-63.

Matsumoto, S., Ikura, K., Ueda, M., and Sasaki, R. (1163). Characterization of a human glycoprotein (erythropoietin) produced in cultured tobacco cells. Plant Molecular Biology 27, 1163-1172.

Melo, N. S., Nimtz, M., Conradt, H. S., Fevereiro, P. S., and Costa, J. (1997). Identification of the human Lewis (a) carbohydrate motif in a secretory peroxidase from a plant cell suspension culture (*Vaccinium myrtillus* L.). FEBS Lett 415, 186-91.

Palacpac, N. Q., Kimura, Y., Fuijyama, K., Yoshida, T., and Seki, T. (1999). Structures of N-linked oligosaccharides of glycoproteins from tobacco BY2 suspension cultured cells. Biosci Biotechnol Biochem 63, 35-9.

Palacpac, N. Q., Yoshida, S., Sakai, H., Kimura, Y., Fuijyama, K., Yoshida, T., and Seki, T. (1999). Stable expression of human beta 1,4-galactosyltransferase in plant cells modifies N-linked glycosylation patterns. Proc Natl Acad Sci USA 96, 4692-7.

Rayon, C., Cabanes Macheteau, M., Loutelier Bourhis, C., Salliot Maire, I., Lemoine, J., Reiter, W. D. Lerouge, P., and Faye, L. (1999). Characterization of N-glycans from *Arabidopsis*. Application to a fucose-deficient mutant. Plant Physiol 119, 725-34.

Saito, K., Noji, M. Ohmori, S., Imai, Y., and Murakoshi, I. (1991). Integration and expression of a rabbit liver cytochrome P-450 gene in transgenetic *Nicotiana tabacum*. Proceedings Of The National Academy Of Sciences Of The United States Of America 88, 7041-7045.

Sambrook, J., Fritsch, E. F., and Maniatis, T. (1989). Molecular Cloning: A Laboratory Manual (Plainview, N.Y.: Cold Spring Harbor Lab. Press).

Schachter, H. (1991). The 'yellow brick road' to branched complex N-glycans. Glycobiology 1, 453-61.

Schindler, T., Bergfeld, R., and Schopfer, P. (1995). Arabinogalactan proteins in maize coleoptiles: developmental relationship to cell death during xylem differentiation but not to extention growth. Plant JU 7, 25-36.

Schaper, N. L., Shaper, J. H., Meuth, J. L., Fox, J. L., Chang, H., Kirsch, I. R. and Hollis, G. F. (1986). Bovine galactosyltransferase: identification of a clone by direct immunological screening of a cDNA expression library. Proc Natl Acad Sci USA 83, 1573-7.

Smant, G., Goverse, A., Stokkermans, J. P. W. G., De Boer, J. M., Pomp, H., Zilverentant, J. F. Overmars, H. A. Helder, J., Schots, A. and Baaker, J. (1997) Potato root diffusate-induced secretion of soluble, basic proteins originating from the subventral esophageal glands of potato cyst nematodes. Phytopathology 87, 839-845.

Stanley, P., and Ioffe, E, (1995). Glycosyltransferase mutants: key to new insights in glycobiology. Faseb j 9, 1436-44.

Stanley, P., Raju, T. S., and Bhaumik, M. (1996). CHO cells provide access to novel N-glycans and developmentally regulated glycosyltransferases. Glycobiology 6, 695-9.

Thanavala, Y., Yang, Y. F., Lyons, P., Mason, H. S., and Arntzen, C. (1995). Immunbgenicity of transgenetic plant-derived hepatitis B surface antigen. Proceedings of the National Academy of Sciences of the United States of America 92, 3358-3361.

van Engelen, F. A., Molthoff, J. W., Conner, A. J., Nap, J. P., Pereira, A., and Stiekema, W. J. (1995). pBINPLUS: an improved plant transformation vector based on pBIN19. Transgenetic Res 4, 288-90.

van Engelen, F. A., Schouten, A., Molthoff, J. W., Roosein, J. Salinas, J., Dirkse, W. G., Schots, A., Bakker, J., Gommers, F. J., Jongsma, M. A., and et al. (1994). Coordinate expression of antibody subunit genes yields high levels of functional antibodies in roots of transgenetic tobacco. Plant Mol Biol. 26, 1701-10.

von Schaewen, A., Sturm, A., O'Neill, J., and Chrispeels, M. J. (1993). Isolation of a mutant *Arabidopsis* plant that lacks N-acetyl glucosaminyl transferase I and is unable to synthesize Golgi-modified complex N-linked glycans. Plant Physiol 102, 1109-18.

Yamaguchi, N., and Fukuda, M. N. (1995). Golgi retention mechanism of beta-1,4-galactosyltransferase. Membrane-spanning domain-dependent homodimerization and association with alpha- and beta-tubulins. J Biol Chem 270, 12170-6.

We claim:

1. A transgenic plant or plant cell comprising six exogenous genes encoding (i) a mammalian β1,4-galactosyltransferase, (ii) a mammalian sialyl transferase, (iii) a mammalian GlcNAc-2 epimerase,)iv) a bacterial NeuAc synthase, (v) a mammalian CMP-NeuAc synthetase, and (vi) a mammalian CMP-NeuAc transporter, wherein the transgenic plant produces a glycoprotein comprising a complex N-linked glycan, in which a galactose residue is attached to a N-acetylglucosamine residue and a sialic acid residue is attached to the galactose residue.

2. The transgenic plant or plant cell of claim 1, wherein the mammalian β1,4 galactosyltransferase is a human β1,4-galactosyltransferase.

3. The transgenic plant or plant cell of claim 1, wherein the complex N-linked glycan is devoid of xylose residues.

4. The transgenic plant or plant cell of claim 1, wherein the complex N-linked glycan is devoid of fucose residues.

5. The transgenic plant or plant cell of claim 1, wherein the plant or plant cell belongs to a genus selected from the group consisting of *Nicotiana, Sprirodella, Wolffia, Wolffiella*, and *Lemna*.

6. The transgenic plant or plant cell of claim 1, wherein the plant or plant cell is selected from the group consisting of tobacco, *Arabidopsis thaliana,* duckweed, corn, potato, and tomato.

7. The transgenic plant or plant cell of claim 1, wherein the plant or plant cell further comprises another exogenous gene encoding a glycoprotein, to which the complex N-linked glycan is attached.

8. The transgenic plant or plant cell of claim 7, wherein the other glycoprotein is a mammalian glycoprotein.

9. The transgenic plant or plant cell of claim 8, wherein the other mammalian glycoprotein is an antibody, a hormone, an enzyme, or a cellular adhesion molecule.

10. The transgenic plant or plant cell of claim 1, wherein the GlcNAc-2 epimerase is from pig, the NeuAc synthase is from clostridium, the CMP-NeuAc synthetase is from mouse, the CMP-NeuAc transporter is from human, the sialyl transferase is from human, and the β1,4-galactosyltransferase is from human.

11. The transgenic plant or plant cell of claim 7, wherein the GlcNAc-2 epimerase is from pig, the NeuAc synthase is from clostridium, the CMP-NeuAc synthetase is from mouse, the CMP-NeuAc transporter is from human, the sialyl transferase is from human, and the β1,4-galactosyltransferase is from human.

12. A method of producing an exogenous glycoprotein in a plant or plant cell, the method comprising:
cultivating the plant or plant cell of claim 7; and
harvesting the plant or plant cells thus cultivated for isolation of the exogenous glycoprotein,
wherein the exogenous glycoprotein is attached with a complex N-linked glycan, in which a galactose residue is attached to a N-acetylglucosamine residue and a sialic acid residue is attached to the galactose residue.

13. The method of claim 12, further comprising isolating the exogenous glycoprotein.

* * * * *